(12) United States Patent
Walberg et al.

(10) Patent No.: US 8,870,867 B2
(45) Date of Patent: Oct. 28, 2014

(54) ARTICULABLE ELECTROSURGICAL INSTRUMENT WITH A STABILIZABLE ARTICULATION ACTUATOR

(75) Inventors: Erik Walberg, Redwood City, CA (US); Lawrence Kerver, Los Gatos, CA (US); Brian Tang, Fremont, CA (US); Brandon Loudermilk, San Francisco, CA (US)

(73) Assignee: Aesculap AG, Tuttlingen (DE)

(*) Notice: Subject to any disclaimer, the term of this patent is extended or adjusted under 35 U.S.C. 154(b) by 872 days.

(21) Appl. No.: 13/070,391

(22) Filed: Mar. 23, 2011

(65) Prior Publication Data

US 2011/0230875 A1 Sep. 22, 2011

Related U.S. Application Data

(63) Continuation-in-part of application No. 12/027,231, filed on Feb. 6, 2008.

(60) Provisional application No. 61/382,868, filed on Sep. 14, 2010.

(51) Int. Cl.

| A61B 18/12 | (2006.01) |
|---|---|
| *A61B 17/29* | (2006.01) |
| *A61B 17/295* | (2006.01) |
| A61B 17/00 | (2006.01) |
| A61B 19/00 | (2006.01) |
| A61B 18/14 | (2006.01) |
| A61B 18/00 | (2006.01) |

(52) U.S. Cl.
CPC ... *A61B 18/1445* (2013.01); *A61B 2017/00327* (2013.01); *A61B 2017/003* (2013.01);

(Continued)

(58) Field of Classification Search
USPC .................. 606/27, 34, 41, 51, 52
See application file for complete search history.

(56) References Cited

U.S. PATENT DOCUMENTS

| 3,356,408 A | 12/1967 | Stutz |
|---|---|---|
| 3,527,224 A | 9/1970 | Rabinowitz |

(Continued)

FOREIGN PATENT DOCUMENTS

| CA | 2061215 A1 | 8/1992 |
|---|---|---|
| CN | 1826083 A | 8/2006 |

(Continued)

OTHER PUBLICATIONS

European Application Serial No. 09707446.2, Supplementary European Search Report mailed Oct. 9, 2012.

(Continued)

*Primary Examiner* — Michael Peffley
*Assistant Examiner* — Daniel Fowler
(74) *Attorney, Agent, or Firm* — RatnerPrestia

(57) ABSTRACT

Embodiments of the technology provide an articulable electrosurgical instrument and methods of performing electrosurgery with an articulating capability. The electrosurgical instrument includes an elongated shaft having an end effector associated with a distal end thereof that is able to deliver energy to a target tissue site. An articulable joint is positioned between that shaft and the end effector. Articulation of the articulable joint is controlled by a stabilizable articulation actuator, which may include a rotatably stabilizable disk residing within a well. The end effector may take the form of forceps including an upper and a lower jaw; the jaws are configured to grasp target tissue and to deliver energy, such as radiofrequency energy. In some of these instruments, the end effector is adapted to seal tissue by the application of radiofrequency energy, and then to cut through the sealed tissue portion.

35 Claims, 21 Drawing Sheets

(52) U.S. Cl.
CPC . *A61B 2019/4857* (2013.01); *A61B 2018/1455* (2013.01); *A61B 17/29* (2013.01); *A61B 2018/1412* (2013.01); *A61B 2017/2927* (2013.01); *A61B 17/295* (2013.01); *A61B 2017/2933* (2013.01); *A61B 2017/2923* (2013.01); *A61B 2017/2946* (2013.01); *A61B 2019/2246* (2013.01); *A61B 2018/0063* (2013.01)
USPC ............................................. 606/51; 606/52

(56) References Cited

U.S. PATENT DOCUMENTS

| | | |
|---|---|---|
| 3,709,215 A | 1/1973 | Richmond |
| 3,742,955 A | 7/1973 | Battista et al. |
| 3,845,771 A | 11/1974 | Vise |
| 3,920,021 A | 11/1975 | Hiltebrandt |
| 3,970,088 A | 7/1976 | Morrison |
| 4,018,230 A | 4/1977 | Ochiai et al. |
| 4,041,952 A | 8/1977 | Morrison, Jr. et al. |
| 4,072,153 A | 2/1978 | Swartz |
| 4,094,320 A | 6/1978 | Newton et al. |
| 4,231,372 A | 11/1980 | Newton |
| 4,492,231 A | 1/1985 | Auth |
| 4,532,924 A | 8/1985 | Auth et al. |
| 4,590,934 A | 5/1986 | Malis et al. |
| 4,671,274 A | 6/1987 | Sorochenko |
| 4,972,846 A | 11/1990 | Owens et al. |
| 4,976,717 A | 12/1990 | Boyle |
| 4,979,948 A | 12/1990 | Geddes et al. |
| 4,998,527 A | 3/1991 | Meyer |
| 5,037,379 A | 8/1991 | Clayman et al. |
| 5,041,101 A | 8/1991 | Seder et al. |
| 5,059,782 A | 10/1991 | Fukuyama |
| 5,078,736 A | 1/1992 | Behl |
| 5,108,408 A | 4/1992 | Lally |
| 5,133,713 A | 7/1992 | Huang et al. |
| 5,151,102 A | 9/1992 | Kamiyama et al. |
| 5,156,613 A | 10/1992 | Sawyer |
| 5,178,618 A | 1/1993 | Kandarpa |
| 5,190,541 A | 3/1993 | Abele et al. |
| 5,207,691 A | 5/1993 | Nardella |
| 5,217,030 A | 6/1993 | Yoon |
| 5,234,425 A | 8/1993 | Fogarty et al. |
| 5,250,074 A | 10/1993 | Wilk et al. |
| 5,267,998 A | 12/1993 | Hagen |
| 5,269,780 A | 12/1993 | Roos |
| 5,269,782 A | 12/1993 | Sutter |
| 5,273,524 A | 12/1993 | Fox et al. |
| 5,277,201 A | 1/1994 | Stern |
| 5,281,216 A | 1/1994 | Klicek |
| 5,282,799 A | 2/1994 | Rydell |
| 5,290,287 A | 3/1994 | Boebel et al. |
| 5,295,990 A | 3/1994 | Levin |
| 5,300,068 A | 4/1994 | Rosar et al. |
| 5,300,087 A | 4/1994 | Knoepfler |
| 5,312,023 A | 5/1994 | Green et al. |
| 5,324,289 A | 6/1994 | Eggers |
| 5,330,471 A | 7/1994 | Eggers |
| 5,330,502 A | 7/1994 | Hassler et al. |
| 5,336,229 A | 8/1994 | Noda |
| 5,336,237 A | 8/1994 | Chin et al. |
| 5,341,807 A | 8/1994 | Nardella |
| 5,342,381 A | 8/1994 | Tidemand |
| 5,352,223 A | 10/1994 | McBrayer et al. |
| 5,352,235 A | 10/1994 | Koros et al. |
| 5,354,336 A | 10/1994 | Kelman et al. |
| 5,356,408 A | 10/1994 | Rydell |
| 5,374,277 A | 12/1994 | Hassler |
| 5,377,415 A | 1/1995 | Gibson |
| 5,391,166 A | 2/1995 | Eggers |
| 5,395,369 A | 3/1995 | McBrayer et al. |
| 5,396,900 A | 3/1995 | Slater et al. |
| 5,397,320 A | 3/1995 | Essig et al. |
| 5,403,312 A | 4/1995 | Yates et al. |
| 5,417,687 A | 5/1995 | Nardella et al. |
| 5,423,814 A | 6/1995 | Zhu et al. |
| 5,431,676 A | 7/1995 | Dubrul et al. |
| 5,438,302 A | 8/1995 | Goble |
| 5,443,463 A | 8/1995 | Stern et al. |
| 5,443,470 A | 8/1995 | Stern et al. |
| 5,445,638 A | 8/1995 | Rydell et al. |
| 5,447,513 A | 9/1995 | Davison et al. |
| 5,449,355 A | 9/1995 | Rhum et al. |
| 5,456,684 A | 10/1995 | Schmidt |
| 5,458,598 A | 10/1995 | Feinberg et al. |
| 5,462,546 A | 10/1995 | Rydell |
| 5,472,442 A | 12/1995 | Klicek |
| 5,480,399 A | 1/1996 | Hebborn |
| 5,482,054 A | 1/1996 | Slater et al. |
| 5,484,435 A | 1/1996 | Fleenor et al. |
| 5,484,436 A | 1/1996 | Eggers et al. |
| 5,496,312 A | 3/1996 | Klicek |
| 5,496,317 A | 3/1996 | Goble et al. |
| 5,514,134 A | 5/1996 | Rydell et al. |
| 5,520,698 A | 5/1996 | Koh |
| 5,531,744 A | 7/1996 | Nardella et al. |
| 5,540,684 A | 7/1996 | Hassler, Jr. |
| 5,540,685 A | 7/1996 | Parins et al. |
| 5,542,945 A | 8/1996 | Fritzsch |
| 5,549,637 A | 8/1996 | Crainich |
| 5,556,397 A | 9/1996 | Long et al. |
| 5,558,100 A | 9/1996 | Cox |
| 5,558,671 A | 9/1996 | Yates |
| 5,562,700 A | 10/1996 | Huitema et al. |
| 5,562,701 A | 10/1996 | Huitema et al. |
| 5,562,702 A | 10/1996 | Huitema et al. |
| 5,562,720 A | 10/1996 | Stern et al. |
| 5,569,243 A | 10/1996 | Kortenbach et al. |
| 5,571,100 A | 11/1996 | Goble et al. |
| 5,573,535 A | 11/1996 | Viklund |
| 5,578,052 A | 11/1996 | Koros et al. |
| 5,599,350 A | 2/1997 | Schulze et al. |
| 5,601,224 A | 2/1997 | Bishop et al. |
| 5,603,700 A | 2/1997 | Daneshvar |
| 5,603,711 A | 2/1997 | Parins et al. |
| 5,611,803 A | 3/1997 | Heaven et al. |
| 5,624,452 A | 4/1997 | Yates |
| 5,637,110 A | 6/1997 | Pennybacker et al. |
| 5,637,111 A | 6/1997 | Sutcu et al. |
| 5,653,692 A | 8/1997 | Masterson et al. |
| 5,658,281 A | 8/1997 | Heard |
| 5,662,662 A | 9/1997 | Bishop et al. |
| 5,662,676 A | 9/1997 | Koninckx |
| 5,665,085 A | 9/1997 | Nardella |
| 5,665,100 A | 9/1997 | Yoon |
| 5,667,526 A | 9/1997 | Levin |
| 5,669,907 A | 9/1997 | Platt, Jr. et al. |
| 5,673,840 A | 10/1997 | Schulze et al. |
| 5,673,841 A | 10/1997 | Schulze et al. |
| 5,674,184 A | 10/1997 | Hassler, Jr. |
| 5,674,220 A | 10/1997 | Fox et al. |
| 5,675,184 A | 10/1997 | Matsubayashi et al. |
| 5,680,982 A | 10/1997 | Schulze et al. |
| 5,681,282 A | 10/1997 | Eggers et al. |
| 5,683,385 A | 11/1997 | Kortenbach et al. |
| 5,683,388 A | 11/1997 | Slater |
| 5,688,270 A | 11/1997 | Yates et al. |
| 5,693,051 A | 12/1997 | Schulze et al. |
| 5,697,949 A | 12/1997 | Giurtino et al. |
| 5,700,261 A | 12/1997 | Brinkerhoff |
| 5,702,390 A | 12/1997 | Austin et al. |
| 5,704,534 A | 1/1998 | Huitema et al. |
| 5,707,369 A | 1/1998 | Vaitekunas et al. |
| 5,709,680 A | 1/1998 | Yates et al. |
| 5,713,896 A | 2/1998 | Nardella |
| 5,715,832 A | 2/1998 | Koblish et al. |
| 5,718,703 A | 2/1998 | Chin |
| 5,720,719 A | 2/1998 | Edwards et al. |
| 5,728,143 A | 3/1998 | Gough et al. |
| 5,733,283 A | 3/1998 | Malis et al. |
| 5,735,289 A | 4/1998 | Pfeffer et al. |
| 5,735,848 A | 4/1998 | Yates et al. |
| 5,735,849 A | 4/1998 | Baden et al. |

(56) References Cited

U.S. PATENT DOCUMENTS

| | | |
|---|---|---|
| 5,741,285 A | 4/1998 | McBrayer et al. |
| 5,746,750 A | 5/1998 | Prestel et al. |
| 5,749,895 A | 5/1998 | Sawyer et al. |
| 5,755,717 A | 5/1998 | Yates et al. |
| 5,766,196 A | 6/1998 | Griffiths |
| 5,776,130 A | 7/1998 | Buysse et al. |
| 5,788,662 A | 8/1998 | Antanavich et al. |
| 5,797,941 A | 8/1998 | Schulze et al. |
| 5,810,811 A | 9/1998 | Yates et al. |
| 5,817,091 A | 10/1998 | Nardella et al. |
| 5,817,092 A | 10/1998 | Behl |
| 5,823,066 A | 10/1998 | Huitema et al. |
| 5,833,689 A | 11/1998 | Long |
| 5,836,990 A | 11/1998 | Li |
| 5,840,077 A | 11/1998 | Rowden et al. |
| 5,855,576 A | 1/1999 | LeVeen et al. |
| 5,860,975 A | 1/1999 | Goble et al. |
| 5,891,142 A | 4/1999 | Eggers et al. |
| 5,893,835 A | 4/1999 | Witt et al. |
| 5,893,874 A | 4/1999 | Bourque et al. |
| 5,931,835 A | 8/1999 | Mackey |
| 5,931,836 A | 8/1999 | Hatta et al. |
| 5,954,720 A | 9/1999 | Wilson et al. |
| 5,976,128 A | 11/1999 | Schilling et al. |
| 5,979,453 A | 11/1999 | Savage et al. |
| 6,003,517 A | 12/1999 | Sheffield et al. |
| 6,004,319 A | 12/1999 | Goble et al. |
| 6,030,384 A | 2/2000 | Nezhat |
| 6,050,993 A | 4/2000 | Tu et al. |
| 6,050,995 A | 4/2000 | Durgin |
| 6,056,744 A | 5/2000 | Edwards |
| 6,059,766 A | 5/2000 | Greff |
| 6,059,782 A | 5/2000 | Novak et al. |
| 6,066,139 A | 5/2000 | Ryan et al. |
| 6,068,626 A | 5/2000 | Harrington et al. |
| 6,071,281 A | 6/2000 | Burnside et al. |
| 6,074,386 A | 6/2000 | Goble et al. |
| 6,077,287 A | 6/2000 | Taylor |
| 6,086,586 A | 7/2000 | Hooven |
| 6,090,106 A | 7/2000 | Goble et al. |
| 6,093,186 A | 7/2000 | Goble |
| 6,096,037 A | 8/2000 | Mulier et al. |
| 6,099,550 A | 8/2000 | Yoon |
| 6,123,701 A | 9/2000 | Nezhat |
| H1904 H | 10/2000 | Yates et al. |
| 6,142,992 A | 11/2000 | Cheng et al. |
| 6,152,920 A | 11/2000 | Thompson et al. |
| 6,152,932 A | 11/2000 | Ternstrom |
| 6,162,220 A | 12/2000 | Nezhat |
| 6,174,309 B1 | 1/2001 | Wrublewski et al. |
| 6,179,832 B1 | 1/2001 | Jones et al. |
| 6,203,541 B1 | 3/2001 | Keppel |
| 6,203,542 B1 | 3/2001 | Ellsberry et al. |
| 6,206,877 B1 | 3/2001 | Kese et al. |
| 6,210,406 B1 | 4/2001 | Webster |
| 6,212,426 B1 | 4/2001 | Swanson |
| 6,217,894 B1 | 4/2001 | Sawhney et al. |
| 6,228,084 B1 | 5/2001 | Kirwan, Jr. |
| 6,234,178 B1 | 5/2001 | Goble et al. |
| 6,241,139 B1 | 6/2001 | Milliman et al. |
| 6,245,069 B1 | 6/2001 | Gminder |
| 6,254,601 B1 | 7/2001 | Burbank et al. |
| 6,258,085 B1 | 7/2001 | Eggleston |
| 6,277,114 B1 | 8/2001 | Bullivant et al. |
| 6,283,963 B1 | 9/2001 | Regula |
| 6,287,304 B1 | 9/2001 | Eggers et al. |
| 6,290,715 B1 | 9/2001 | Sharkey et al. |
| 6,293,942 B1 | 9/2001 | Goble et al. |
| 6,293,946 B1 | 9/2001 | Thorne |
| 6,296,636 B1 | 10/2001 | Cheng et al. |
| 6,312,430 B1 | 11/2001 | Wilson et al. |
| 6,322,494 B1 | 11/2001 | Bullivant et al. |
| 6,327,505 B1 | 12/2001 | Medhkour et al. |
| 6,334,861 B1 | 1/2002 | Chandler et al. |
| 6,350,274 B1 | 2/2002 | Li |
| 6,361,559 B1 | 3/2002 | Houser et al. |
| 6,364,879 B1 | 4/2002 | Chen et al. |
| 6,371,956 B1 | 4/2002 | Wilson et al. |
| 6,391,024 B1 | 5/2002 | Sun et al. |
| 6,391,029 B1 | 5/2002 | Hooven et al. |
| 6,398,779 B1 | 6/2002 | Buysse et al. |
| 6,398,781 B1 | 6/2002 | Goble et al. |
| H2037 H | 7/2002 | Yates et al. |
| 6,416,509 B1 | 7/2002 | Goble et al. |
| 6,428,550 B1 | 8/2002 | Vargas et al. |
| 6,436,096 B1 | 8/2002 | Hareyama |
| 6,464,702 B2 | 10/2002 | Schulze et al. |
| 6,485,486 B1 | 11/2002 | Trembly et al. |
| 6,485,489 B2 | 11/2002 | Teirstein et al. |
| 6,491,690 B1 | 12/2002 | Goble et al. |
| 6,494,881 B1 | 12/2002 | Bales et al. |
| 6,500,176 B1 | 12/2002 | Truckai et al. |
| 6,514,252 B2 | 2/2003 | Nezhat et al. |
| 6,517,530 B1 | 2/2003 | Kleven |
| 6,520,185 B1 | 2/2003 | Bommannan et al. |
| 6,533,784 B2 | 3/2003 | Truckai et al. |
| 6,546,933 B1 | 4/2003 | Yoon |
| 6,554,829 B2 | 4/2003 | Schulze et al. |
| 6,564,806 B1 | 5/2003 | Fogarty et al. |
| 6,565,560 B1 | 5/2003 | Goble et al. |
| 6,565,561 B1 | 5/2003 | Goble et al. |
| 6,584,360 B2 | 6/2003 | Francischelli et al. |
| 6,610,074 B2 | 8/2003 | Santilli |
| 6,616,654 B2 | 9/2003 | Mollenauer |
| 6,616,659 B1 | 9/2003 | de la Torre et al. |
| 6,619,529 B2 | 9/2003 | Green et al. |
| 6,622,731 B2 * | 9/2003 | Daniel et al. ............... 128/898 |
| 6,623,482 B2 | 9/2003 | Pendekanti et al. |
| 6,626,901 B1 | 9/2003 | Treat et al. |
| 6,645,198 B1 | 11/2003 | Bommannan et al. |
| 6,645,201 B1 | 11/2003 | Utley et al. |
| 6,648,839 B2 | 11/2003 | Manna et al. |
| 6,652,518 B2 | 11/2003 | Wellman et al. |
| 6,656,177 B2 | 12/2003 | Truckai et al. |
| 6,666,859 B1 | 12/2003 | Fleenor et al. |
| 6,673,085 B1 | 1/2004 | Berg |
| 6,676,660 B2 | 1/2004 | Wampler et al. |
| 6,682,526 B1 | 1/2004 | Jones et al. |
| 6,682,527 B2 | 1/2004 | Strul |
| 6,695,840 B2 | 2/2004 | Schulze |
| 6,699,245 B2 | 3/2004 | Dinger et al. |
| 6,719,754 B2 | 4/2004 | Underwood et al. |
| 6,722,371 B1 | 4/2004 | Fogarty et al. |
| 6,736,814 B2 | 5/2004 | Manna et al. |
| 6,743,229 B2 | 6/2004 | Buysse et al. |
| 6,746,488 B1 | 6/2004 | Bales |
| 6,752,154 B2 | 6/2004 | Fogarty et al. |
| 6,752,803 B2 | 6/2004 | Goldman et al. |
| 6,770,070 B1 | 8/2004 | Balbierz |
| 6,770,072 B1 | 8/2004 | Truckai et al. |
| 6,808,525 B2 | 10/2004 | Latterell et al. |
| 6,817,974 B2 | 11/2004 | Cooper et al. |
| 6,821,273 B2 | 11/2004 | Mollenauer |
| 6,837,888 B2 | 1/2005 | Ciarrocca et al. |
| 6,840,938 B1 | 1/2005 | Morley et al. |
| 6,843,789 B2 | 1/2005 | Goble |
| 6,852,108 B2 | 2/2005 | Barry et al. |
| 6,889,089 B2 | 5/2005 | Behl et al. |
| 6,893,435 B2 | 5/2005 | Goble |
| 6,896,672 B1 | 5/2005 | Eggers et al. |
| 6,896,673 B2 | 5/2005 | Hooven |
| 6,905,506 B2 | 6/2005 | Burbank et al. |
| 6,913,579 B2 | 7/2005 | Truckai et al. |
| 6,918,907 B2 | 7/2005 | Kelly et al. |
| 6,918,909 B2 | 7/2005 | Ohyama et al. |
| 6,923,803 B2 | 8/2005 | Goble |
| 6,926,712 B2 | 8/2005 | Phan |
| 6,929,642 B2 | 8/2005 | Xiao et al. |
| 6,936,048 B2 | 8/2005 | Hurst |
| 6,939,346 B2 | 9/2005 | Kannenberg et al. |
| 6,953,461 B2 | 10/2005 | McClurken et al. |
| 6,981,628 B2 | 1/2006 | Wales |
| 7,033,356 B2 | 4/2006 | Latterell et al. |
| 7,063,699 B2 | 6/2006 | Hess et al. |

(56) References Cited

U.S. PATENT DOCUMENTS

| | | |
|---|---|---|
| 7,090,637 B2 | 8/2006 | Danitz et al. |
| 7,090,673 B2 | 8/2006 | Dycus et al. |
| 7,090,685 B2 | 8/2006 | Kortenbach et al. |
| 7,094,202 B2 * | 8/2006 | Nobis et al. .............. 600/131 |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,118,587 B2 | 10/2006 | Dycus et al. |
| 7,125,409 B2 | 10/2006 | Truckai et al. |
| 7,137,980 B2 | 11/2006 | Buysse et al. |
| 7,159,750 B2 | 1/2007 | Racenet et al. |
| 7,166,102 B2 | 1/2007 | Fleenor et al. |
| 7,169,146 B2 | 1/2007 | Truckai et al. |
| 7,179,254 B2 | 2/2007 | Pendekanti et al. |
| 7,195,627 B2 | 3/2007 | Amoah et al. |
| 7,208,005 B2 * | 4/2007 | Frecker et al. ............ 606/205 |
| 7,220,260 B2 | 5/2007 | Fleming et al. |
| 7,238,195 B2 | 7/2007 | Viola |
| 7,250,048 B2 | 7/2007 | Francischelli et al. |
| 7,267,677 B2 | 9/2007 | Johnson et al. |
| 7,270,664 B2 | 9/2007 | Johnson et al. |
| 7,276,068 B2 | 10/2007 | Johnson et al. |
| 7,278,991 B2 | 10/2007 | Morris et al. |
| 7,291,143 B2 | 11/2007 | Swanson |
| 7,364,577 B2 | 4/2008 | Wham et al. |
| 7,367,972 B2 | 5/2008 | Francischelli et al. |
| 7,410,483 B2 | 8/2008 | Danitz et al. |
| 7,494,039 B2 | 2/2009 | Racenet et al. |
| 7,506,790 B2 | 3/2009 | Shelton, IV et al. |
| 7,540,872 B2 | 6/2009 | Schechter et al. |
| 7,549,564 B2 | 6/2009 | Boudreaux |
| 7,624,902 B2 | 12/2009 | Marczyk et al. |
| 7,641,651 B2 | 1/2010 | Nezhat et al. |
| 7,703,653 B2 | 4/2010 | Shah et al. |
| 7,794,461 B2 | 9/2010 | Eder et al. |
| 7,803,156 B2 | 9/2010 | Eder et al. |
| 7,862,565 B2 | 1/2011 | Eder et al. |
| 7,942,874 B2 | 5/2011 | Eder et al. |
| 2001/0029367 A1 | 10/2001 | Fleenor et al. |
| 2002/0062123 A1 | 5/2002 | McClurken et al. |
| 2002/0062136 A1 | 5/2002 | Hillstead et al. |
| 2002/0107514 A1 | 8/2002 | Hooven |
| 2002/0124853 A1 | 9/2002 | Burbank et al. |
| 2002/0128643 A1 | 9/2002 | Simpson et al. |
| 2002/0151882 A1 | 10/2002 | Marko et al. |
| 2002/0177848 A1 | 11/2002 | Truckai et al. |
| 2002/0183738 A1 | 12/2002 | Chee et al. |
| 2003/0078577 A1 | 4/2003 | Truckai et al. |
| 2003/0144652 A1 | 7/2003 | Baker et al. |
| 2003/0144653 A1 | 7/2003 | Francischelli et al. |
| 2003/0158547 A1 | 8/2003 | Phan |
| 2003/0171745 A1 | 9/2003 | Francischelli et al. |
| 2003/0216726 A1 | 11/2003 | Eggers et al. |
| 2003/0229344 A1 | 12/2003 | Dycus et al. |
| 2003/0236549 A1 | 12/2003 | Bonadio et al. |
| 2004/0006339 A1 | 1/2004 | Underwood et al. |
| 2004/0010245 A1 | 1/2004 | Cerier et al. |
| 2004/0068274 A1 | 4/2004 | Hooven |
| 2004/0097919 A1 | 5/2004 | Wellman et al. |
| 2004/0122423 A1 | 6/2004 | Dycus et al. |
| 2004/0143263 A1 | 7/2004 | Schechter et al. |
| 2004/0199226 A1 | 10/2004 | Shadduck |
| 2004/0236320 A1 | 11/2004 | Protsenko et al. |
| 2005/0010212 A1 | 1/2005 | McClurken et al. |
| 2005/0015085 A1 | 1/2005 | McClurken et al. |
| 2005/0021026 A1 | 1/2005 | Baily |
| 2005/0021027 A1 | 1/2005 | Shields et al. |
| 2005/0033276 A1 | 2/2005 | Adachi |
| 2005/0033277 A1 | 2/2005 | Clague et al. |
| 2005/0033278 A1 | 2/2005 | McClurken et al. |
| 2005/0070895 A1 | 3/2005 | Ryan et al. |
| 2005/0070978 A1 | 3/2005 | Bek et al. |
| 2005/0090819 A1 | 4/2005 | Goble |
| 2005/0096645 A1 | 5/2005 | Wellman et al. |
| 2005/0096694 A1 | 5/2005 | Lee |
| 2005/0107781 A1 | 5/2005 | Ostrovsky et al. |
| 2005/0107784 A1 | 5/2005 | Moses et al. |
| 2005/0113817 A1 | 5/2005 | Isaacson et al. |
| 2005/0113820 A1 | 5/2005 | Goble et al. |
| 2005/0119654 A1 | 6/2005 | Swanson et al. |
| 2005/0131390 A1 | 6/2005 | Heinrich et al. |
| 2005/0149073 A1 | 7/2005 | Arani et al. |
| 2005/0171533 A1 | 8/2005 | Latterell et al. |
| 2005/0187561 A1 | 8/2005 | Lee-Sepsick et al. |
| 2005/0192633 A1 | 9/2005 | Montpetit |
| 2005/0196421 A1 | 9/2005 | Hunter et al. |
| 2005/0203500 A1 | 9/2005 | Saadat et al. |
| 2005/0203504 A1 | 9/2005 | Wham et al. |
| 2005/0209664 A1 | 9/2005 | Hunter et al. |
| 2005/0226682 A1 | 10/2005 | Chersky et al. |
| 2005/0256522 A1 | 11/2005 | Francischelli et al. |
| 2005/0256524 A1 | 11/2005 | Long et al. |
| 2005/0261676 A1 | 11/2005 | Hall et al. |
| 2006/0011699 A1 * | 1/2006 | Olson et al. .............. 227/180.1 |
| 2006/0025765 A1 | 2/2006 | Landman et al. |
| 2006/0025812 A1 | 2/2006 | Shelton, IV |
| 2006/0041254 A1 | 2/2006 | Francischelli et al. |
| 2006/0052778 A1 | 3/2006 | Chapman et al. |
| 2006/0052779 A1 | 3/2006 | Hammill |
| 2006/0064084 A1 | 3/2006 | Haemmerich et al. |
| 2006/0079872 A1 | 4/2006 | Eggleston |
| 2006/0167451 A1 | 7/2006 | Cropper |
| 2006/0190029 A1 | 8/2006 | Wales |
| 2006/0199999 A1 | 9/2006 | Ikeda et al. |
| 2006/0217709 A1 | 9/2006 | Couture et al. |
| 2006/0226196 A1 | 10/2006 | Hueil et al. |
| 2006/0229665 A1 | 10/2006 | Wales et al. |
| 2006/0253117 A1 | 11/2006 | Hovda et al. |
| 2006/0258954 A1 | 11/2006 | Timberlake et al. |
| 2006/0259035 A1 | 11/2006 | Nezhat et al. |
| 2006/0271037 A1 | 11/2006 | Maroney et al. |
| 2006/0271042 A1 | 11/2006 | Latterell et al. |
| 2006/0287674 A1 | 12/2006 | Ginn et al. |
| 2006/0289602 A1 | 12/2006 | Wales et al. |
| 2006/0293655 A1 | 12/2006 | Sartor |
| 2007/0005061 A1 | 1/2007 | Eder et al. |
| 2007/0062017 A1 | 3/2007 | Dycus et al. |
| 2007/0073340 A1 | 3/2007 | Shelton, IV et al. |
| 2007/0128174 A1 | 6/2007 | Kleinsek et al. |
| 2007/0129726 A1 | 6/2007 | Eder et al. |
| 2007/0173804 A1 | 7/2007 | Wham et al. |
| 2007/0173805 A1 | 7/2007 | Weinberg et al. |
| 2007/0173811 A1 | 7/2007 | Couture et al. |
| 2007/0179497 A1 | 8/2007 | Eggers et al. |
| 2007/0185482 A1 | 8/2007 | Eder et al. |
| 2007/0185518 A1 | 8/2007 | Hassier, Jr. |
| 2007/0244538 A1 | 10/2007 | Eder et al. |
| 2007/0250113 A1 | 10/2007 | Hegeman et al. |
| 2007/0265613 A1 | 11/2007 | Edelstein et al. |
| 2007/0282318 A1 | 12/2007 | Spooner et al. |
| 2007/0282320 A1 | 12/2007 | Buysse et al. |
| 2008/0172052 A1 | 7/2008 | Eder et al. |
| 2008/0188844 A1 | 8/2008 | McGreevy et al. |
| 2008/0195093 A1 | 8/2008 | Couture et al. |
| 2008/0221565 A1 | 9/2008 | Eder et al. |
| 2008/0228179 A1 | 9/2008 | Eder et al. |
| 2008/0275446 A1 | 11/2008 | Messerly |
| 2008/0308607 A1 | 12/2008 | Timm et al. |
| 2009/0138006 A1 | 5/2009 | Bales et al. |
| 2009/0157071 A1 | 6/2009 | Wham et al. |
| 2009/0157072 A1 | 6/2009 | Wham et al. |
| 2009/0157075 A1 | 6/2009 | Wham et al. |
| 2009/0182323 A1 | 7/2009 | Eder et al. |
| 2009/0198272 A1 | 8/2009 | Kerver et al. |
| 2009/0209953 A1 | 8/2009 | Schoenman |
| 2009/0240245 A1 | 9/2009 | Deville et al. |
| 2009/0299367 A1 | 12/2009 | Ginnebaugh et al. |
| 2010/0042093 A9 | 2/2010 | Wham et al. |
| 2010/0076427 A1 | 3/2010 | Heard |
| 2010/0094282 A1 | 4/2010 | Kabaya et al. |
| 2010/0280508 A1 | 11/2010 | Eder |

(56) References Cited

U.S. PATENT DOCUMENTS

| | | |
|---|---|---|
| 2010/0298823 A1 | 11/2010 | Cao et al. |
| 2011/0202058 A1 | 8/2011 | Eder |

FOREIGN PATENT DOCUMENTS

| | | |
|---|---|---|
| EP | 0440385 A2 | 8/1991 |
| EP | 0487269 A1 | 5/1992 |
| EP | 0502268 A1 | 9/1992 |
| EP | 0562195 A1 | 9/1993 |
| EP | 0658333 A1 | 6/1995 |
| EP | 0923907 A1 | 6/1999 |
| EP | 0833593 B1 | 2/2001 |
| EP | 0737446 B1 | 12/2002 |
| EP | 0717960 B1 | 2/2003 |
| EP | 0869742 B1 | 5/2003 |
| EP | 0873089 B1 | 10/2003 |
| EP | 0742696 B1 | 11/2003 |
| EP | 1041933 B1 | 3/2004 |
| EP | 1004277 B1 | 7/2004 |
| EP | 0959786 B1 | 9/2004 |
| EP | 0913126 B1 | 10/2004 |
| EP | 0956827 B1 | 10/2004 |
| EP | 1472984 A1 | 11/2004 |
| EP | 1621146 A2 | 2/2006 |
| EP | 1645237 A1 | 4/2006 |
| EP | 0875209 B1 | 5/2006 |
| EP | 1293170 B1 | 6/2006 |
| EP | 1293169 B1 | 7/2006 |
| EP | 1064886 B1 | 8/2006 |
| EP | 1767164 A1 | 3/2007 |
| EP | 1518498 B1 | 12/2007 |
| EP | 1862138 A1 | 12/2007 |
| EP | 1039862 B1 | 5/2008 |
| EP | 1532933 B1 | 5/2008 |
| EP | 1707143 B1 | 6/2008 |
| EP | 1518499 B1 | 8/2008 |
| EP | 1632192 B1 | 3/2009 |
| EP | 1486177 B1 | 8/2009 |
| EP | 1852081 B1 | 8/2009 |
| EP | 1747761 B1 | 10/2009 |
| EP | 2106764 A2 | 10/2009 |
| JP | 2003088534 | 3/2003 |
| JP | 2004049566 | 2/2004 |
| JP | 2005144193 | 6/2005 |
| WO | WO92/22257 A1 | 12/1992 |
| WO | WO93/08754 A1 | 5/1993 |
| WO | WO94/00060 A1 | 1/1994 |
| WO | WO94/26179 A1 | 11/1994 |
| WO | WO95/02371 A2 | 1/1995 |
| WO | WO96/05776 A1 | 2/1996 |
| WO | WO96/16605 A1 | 6/1996 |
| WO | WO96/23449 A1 | 8/1996 |
| WO | WO97/24073 A1 | 7/1997 |
| WO | WO97/24074 A1 | 7/1997 |
| WO | WO98/12999 A2 | 4/1998 |
| WO | WO98/43548 A1 | 10/1998 |
| WO | WO98/53750 A1 | 12/1998 |
| WO | WO99/23933 A2 | 5/1999 |
| WO | WO99/52459 A1 | 10/1999 |
| WO | WO99/56646 A1 | 11/1999 |
| WO | WO00/13192 A1 | 3/2000 |
| WO | WO00/13193 A1 | 3/2000 |
| WO | WO01/12090 A1 | 2/2001 |
| WO | WO01/35846 A1 | 5/2001 |
| WO | WO01/54602 A2 | 8/2001 |
| WO | WO01/58372 A1 | 8/2001 |
| WO | WO01/58373 A1 | 8/2001 |
| WO | WO01/82812 A1 | 11/2001 |
| WO | WO02/24092 A1 | 3/2002 |
| WO | WO02/058542 A2 | 8/2002 |
| WO | WO02/067798 A1 | 9/2002 |
| WO | WO-02080783 A1 | 10/2002 |
| WO | WO03/088806 A2 | 10/2003 |
| WO | WO03/103522 A1 | 12/2003 |
| WO | WO2004/032596 A2 | 4/2004 |
| WO | WO2004/032776 A1 | 4/2004 |
| WO | WO2004/073490 A2 | 9/2004 |
| WO | WO2004/098383 A2 | 11/2004 |
| WO | WO 2004/105578 | 12/2004 |
| WO | WO2005/009213 A2 | 2/2005 |
| WO | WO2005/034729 A2 | 4/2005 |
| WO | WO2005/079901 A1 | 9/2005 |
| WO | WO2005/115251 A1 | 12/2005 |
| WO | WO2006/060431 A1 | 6/2006 |
| WO | WO2007/002227 A2 | 1/2007 |
| WO | WO2007/082061 A2 | 7/2007 |
| WO | WO-2007146842 A2 | 12/2007 |
| WO | WO2008/094554 A2 | 8/2008 |
| WO | WO2008/124112 A1 | 10/2008 |

OTHER PUBLICATIONS

First Office Action for Chinese Application No. CN 200980104230 Dated Jan. 18, 2012 (w/English Language Translation).

(ArthroCare); ArthroCare receives clearance to market coblation-based devices for gynecology and laparoscopic surgery: clearance includes plasma forceps and 21 specific indications; Business Wire; p. 524; Oct. 25, 2001.

(Business Wire); Radiofrequency energy proven effective against leading cause of obstructive sleep apnea; Business Wire; p09140175; Sep. 14, 1998.

(Curon); Curon announces the publication of data supporting durability and effectiveness of STRETTA® system—positive one year follow-up data of U.S. clinical trial published in gastrointestinal endoscopy; PR Newswire; pNYTH10307022002; Feb. 7, 2002.

(Curon); Curon medical announces presentation of positive clinical study results of STRETTA® procedure for gastroesophageal reflux disease (GERD); PR Newswire; pNYW07920032002; Mar. 20, 2002.

(Enable); Enable medical introduces second generation bipolar scissors; Health Industry Today; pNA; Dec. 1998.

(Everest) Everest medical announces introduction of 3mm bipolar forceps; PR Newswire; p1002MNW021; Oct. 2, 1996.

(Everest) Everest medical discusses patent status: forecasts $1 million revenue first quarter: introduces next generation bipolar scissors; PR Newswire; pN/A; Mar. 31, 1994.

(Everest) Everest medical introduces new Quadripolar} cutting forceps at the global congress for gynecologic endoscopy meeting; PR Newswire; p. 8927; Nov. 8, 1999.

(Everest) Everest medical reports record first quarter results: introduces next generation bipolar scissors; PR Newswire; pN/A; Apr. 19, 1994.

(Everest) Quadripolar cutting forceps introduced by Everest Medical; Health Industry Today; vol. 63; No. 1; pNA; Jan. 2000.

(Novare); U.S. patent issued for Novare Surgical Systems Cygnet® surgical clamp: Novare signs multi-year supply agreement with Boston Scientific; PR Newswire; pNA; Sep. 2, 2003.

Aoki et al.; Thoracoscopic resection of the lung with the ultrasonic scalpel; Ann thorac Surg; vol. 67; No. 4; pp. 1181-1183; Apr. 1999.

Bergamaschi et al.; Laparoscopic intracorporeal bowel resection with ultrasound versus electrosurgical dissection; JSLS; vol. 5; No. 1; pp. 17-20; Jan.-Mar. 2001.

Eichfeld et al.; Evaluation of ultracision in lung metastatic surgery; Ann Thorac Surg; vol. 70; No. 4; pp. 1181-1184; Oct. 2000.

ERBE Elektromedizin GmbH; ERBE BiClamp Brochure; http://www.erbe-med.com/erbe/media/Marketingmaterialien/85100-139_ERBE_EN_BiClamp_D024676.pdf; downloaded Jan. 24, 2011; 6 pgs.

Gyrus ACMI (an Olympus Company); PKS Seal (product page); http://www.gyrusacmi.com/user/display.cfm?display=product&pid=9024; downloaded Jan. 24, 2011; 1 page.

Gyrus Medical; Cutting Forceps (Product Information); downloaded Oct. 5, 2005.

Gyrus Medical; LP Scissors (Product Information); downloaded Oct. 5, 2005.

Gyrus Medical; Lyons} Dissecting Forceps (Product Information); downloaded Oct. 5, 2005.

(56) References Cited

OTHER PUBLICATIONS

Gyrus Medical; Micro/Macro-Jaw Forceps (Product Information); downloaded Oct. 5, 2005.

Gyrus Medical; Seal} Open Forceps (Product Information); downloaded Oct. 5, 2005.

Hayashi et al.; Experimental and clinical evaluation of the harmonic scalpel in thoracic surgery; Kurume Med J; vol. 46; No. 1; pp. 25-29; 1999.

Hefni et al.; Safety and efficacy of using the ligasure vessel sealing system for securing the pedicles in vaginal hysterectomy: randomized controlled trial; BJOG; vol. 112; No. 3; pp. 329-333; Mar. 2005.

Heniford et al.; Initial results with an electrothermal bipolar vessel sealer; Surg Endosc; vol. 15; No. 8; pp. 799-801; Aug. 2001.

Johnson & Johnson Gateway, LLC; The Gynecare Versapoint (Product Information); http://jnjgateway.com/home/jhtml?loc=USENG &page=viewContent&id=edea000100001747 &parentid=fc0de00100000334; downloaded Oct. 20, 2005.

Kamat et al.; Superiority of electrocautery over the suture method for achieving cervical cone bed hemostasis; Obstet Gynecol; vol. 102; No. 4; pp. 726-730; Oct. 2003.

Kennedy et al.; High-burst-strength, feedback-controlled bipolar vessel sealing; Surg Endosc; vol. 12; No. 6; pp. 876-878; Jun. 1998.

Kim et al.; Design and fabrication of a locomotive mechanism for capsule-type endoscopes using shape memory alloys (SMAs); IEEE/ASME Trans on Mechatronics; vol. 10; No. 1; pp. 77-86; Feb. 2005.

Kovac; Transvaginal hysterectomy: rationale and surgical approach; Obstet. Gynecol.; vol. 103; pp. 1321-1325; 2004.

Landman et al.; Evaluation of a vessel sealing system, bipolar electrosurgery, harmonic scalpel, . . . in a porcine model; J. urol; vol. 169; No. 2; pp. 697-700; Feb. 2003.

Levy, et al.; Update on hysterectomy: new technology and techniques; A Supp. To OBG Maganagement; Feb. 2003.

Levy, et al.; Use of a new vessel ligation device during vaginal hysterectomy (presentation abstract); presented at FIGO 2000; Washington, D.C.; 2000.

Lin et al.; Application of ultrasonic scalpel in gynecologic operative laparoscopy; Chin Med J (Engl.); vol. 114; No. 12; pp. 1283-1285; Dec. 2001.

Live Tissue Connect Technologies; company profile; (http://www.onemedplace.com/database/compdisplay_print.php?CompanyID=11508); 1 pg.; Oct. 19, 2010 (downloaded Feb. 7, 2011).

Lyons et al.; An innovative bipolar instrument for laparoscopic surgery; JSLS; vol. 9; No. 1; pp. 39-41; Jan.-Mar. 2005.

McClurken et al.; Collagen shrinkage and vessel sealing; Technical brief #300. Dover, NH: Tissue Link Medical; 2001.

Nojarov et al.; High-energy scissors mode; Phys Rev C Nucl Phys; vol. 51; No. 5; pp. 2449-2456; 1995 (http://arxiv.org/abs/nucl-th/9502001v1).

Parikh et al.; Three dimensional virtual reality model of the normal female pelvic floor; Annals of Bimedical Engineering; vol. 32; pp. 292-296; Feb. 2004.

Refractec, Inc.; Medical use of radiofrequency (RF) energy; (http://www.locateadoc.com/Site_Tools/Print.cfm); 2 pgs.; Aug. 23, 2008 (downloaded Feb. 7, 2011).

SAGES 2001 Hands-On Course I—Taking it the next level: advanced laparoscopic techniques; http://wvvw.sages.org/01program/syllabi/ho1/ho1.html#schirme; 24 pgs.; downloaded Oct. 5, 2005.

SAGES 2001 Nurses Program, Session 1; http://sages.org/01program/syllabi/nurse/nurse.html; downloaded Jan. 24, 2011; 5 pgs.

Srisombut et al.; Laparoscopic hysterectomy using laparoscopic coagulating shears: experience of 15 cases; J. Med Assoc Thai; vol. 83; No. 8; pp. 915-920; Aug. 2000.

Surgrx 510(K) Summary (# K031133); Palo Alto, CA; 5 pgs.; Jul. 3, 2003.

Treat; A new thermal device for sealing and dividing blood vessels; http://www.starioninstruments.com/PDFs/Treat.pdf; downloaded Jun. 29, 2005; 2 pgs.

Tyco Healthcare; The LigaSure Vessel Sealing System (Brochure); Apr. 2002; 8 pgs.

Valleylab Products; Valleylab Products—Electrosurgical Forceps: The surgeon's choice for quality and precision (product information); http://www.valleylab.com/product/es/accessories/forceps_over.html; downloaded Oct. 20, 2005.

Valleylab Products; Valleylab Products—Ligasure} vessel sealing system (product information); http://www.valleylab.com/product/vessel_seal/index.html; downloaded Oct. 20, 2005.

Nezhat et al.; U.S. Appl. No. 08/948,282 entitled "Method and systems for organ resection," filed Oct. 9, 1997.

Eder, Joseph C.; U.S. Appl. No. 12/200,798 entitled "Assisted systems and methods for performing transvaginal hysterectomies," filed Aug. 28, 2008.

Koss et al.; U.S. Appl. No. 12/748,229 entitled "Impedance mediated power delivery for electrosurgery," filed Mar. 26, 2010.

Koss et al.; U.S. Appl. No. 12/907,646 entitled "Impedance mediated control of power delivery for electrosurgery," filed Oct. 19, 2010.

Walberg, Erik; U.S. Appl. No. 13/021,633 entitled "Laparoscopic radiofrequency surgical device," filed Feb. 4, 2011.

Van Lue et al.; U.S. Appl. No. 13/110,848 entitled "Electrosurgical tissue sealing augmented with a seal-enhancing composition," filed May 18, 2011.

\* cited by examiner

ARTICULABLE ELECTROSURGICAL INSTRUMENT WITH A STABILIZABLE ARTICULATION ACTUATOR

CROSS-REFERENCE TO RELATED APPLICATIONS

This application is a continuation in part of U.S. patent application Ser. No. 12/027,231 of Kerver et al., entitled "METHOD AND APPARATUS FOR ARTICULATING THE WRIST OF A LAPAROSCOPIC GRASPING INSTRUMENT", filed on Feb. 6, 2008. The present application further claims priority to U.S. Provisional Patent Application No. 61/382,868 of Walberg et al., entitled "ARTICULABLE ELECTROSURGICAL INSTRUMENT", filed on Sep. 14, 2010.

INCORPORATION BY REFERENCE

All publications and patent applications mentioned in this specification are herein incorporated by reference to the same extent as if each individual publication or patent application was specifically and individually indicated to be so incorporated by reference.

FIELD OF THE INVENTION

The technology relates to medical devices for use during laparoscopic procedures. More particularly, the technology relates to an electrosurgical instrument with an articulable joint operable to articulate an end effector.

BACKGROUND OF THE INVENTION

Biopolar electrosurgical instruments apply radiofrequency (RF) energy to a surgical site to cut, ablate, or coagulate tissue. A particular application of these electrosurgical effects is to seal blood vessels or tissue sheets. A typical instrument takes the form of a pair of opposing jaws or forceps, with one or more electrodes on each jaw tip. In an electrosurgical procedure, the electrodes are placed in close proximity to each other as the jaws are closed on a target site such that the path of alternating current between the two electrodes passes through tissue within the target site. The mechanical force exerted by the jaws and the electrical current combine to create the desired surgical effect. By controlling the level of mechanical and electrical parameters, such as the pressure applied by the jaws, the gap distance between electrodes, and the voltage, current, frequency, and duration of the electrosurgical energy applied to the tissue, the surgeon can coagulate, cauterize, or seal tissue toward a therapeutic end.

Electrosurgical procedures can be performed in an open environment, through conventional incisions, or they may be performed laparoscopically, through small incisions, typically 0.5 cm-1.5 cm in length. A laparoscopic procedure may include the use of a telescopic rod lens system that is connected to a video camera and to a fiber optic cable system that conveys light from a cold light source to illuminate the operative field. The laparoscope is typically inserted into a port in the body through a 5 mm or 10 mm cannula to view the operative field. Surgery is performed during a laparoscopic procedure with any of various tools that are typically arranged at the distal end of a shaft and are operable by manipulation of a handle or other actuator positioned at the proximal end of the shaft.

The laparoscopic operating environment is very constrained spatially; improvements with regard to the manipulatability of laparoscopic devices by surgeons, or more particularly, improvements in the range of motion that end effectors for electrosurgical device can achieve would be advantageous in the field.

SUMMARY OF THE INVENTION

Embodiments of the technology provided herein include an articulable electrosurgical instrument and methods of performing electrosurgery with an instrument having an articulating capability. Embodiments of the electrosurgical instrument include an elongated shaft having an end effector associated with a distal end thereof and a handle associated with a proximal end thereof, the end effector being able to deliver radiofrequency energy to a target tissue site. In typical embodiments of the instrument, the end effector may take the form of forceps or a set of jaws, including a first jaw (a lower jaw, for example) and a second jaw (a lower jaw, for example). The set of jaws is configured to grasp target tissue and to deliver energy, such as radiofrequency energy. In some of these instruments, the set of jaws is particularly adapted to seal tissue by the application of radiofrequency energy, and then to cut through the sealed tissue portion with a blade.

Embodiments of the instrument may further include an articulable joint positioned between the shaft and the end effector; the joint is configured to articulate the end effector angularly within an arc of articulation, the articulable joint including at least one pivotable link or flexible element, or alternatively, a set of one of more interconnected pivotable links, disks, or flexing elements. The instrument may further include a stabilizable articulation actuator disposed proximal to the articulable joint. Some embodiments of the instrument may include a shaft rotator or shaft rotating actuator. The shaft rotator may be disposed proximal to the articulable joint, may be disposed generally at a position along a proximal portion of the shaft, and may be associated with the handle portion of the device. In particular embodiments, the stabilizable articulation actuator may be included within or in association with a shaft rotator. The shaft rotator, itself, is configured to rotate the shaft with respect to the handle, and by virtue of rotation of the shaft, the end effector is also rotated. Advantages of the stabilizable articulation actuator include permitting a surgeon to put lateral forces on the end effector, such as when using the end effector to retract tissue, without having to manually operate a knob or other device to lock and later unlock the angular orientation of the end effector. The stabilizable articulation actuator can allow the surgeon to easily move between different articulation angles without a separate locking action, yet the angular orientation of the end effector may be advantageously stabilized in the chosen articulation angle.

The instrument may further include at least two force transfer members or member portions for translating rotational movement of the actuator mechanism into articulating movement of the end effector. The force transfer member are operably connected at their proximal end to the articulation actuator, and operably connected at their distal end through the articulable joint to a proximal portion of the end effector, thereby allowing rotational movement of the articulation actuator to be translated into articulating movement of the end effector. Force transfer members may be of any suitable form, such as wires, cables, rods, strips, or portions thereof that can transfer tension and/or compression forces. Embodiments of the instrument described herein, and examples of embodiments shown in figures will refer to or depict cables, but it should be understood that any suitable force transfer member is included within the scope of the disclosure. The stabilizable articulation actuator may be configured to stabilize the articulable joint at an angle by stabilizing the force transfer cables, the stabilized angle of the articulable joint being one of a set of angles spaced apart at intervals within the arc of joint articulation.

In some embodiments of the instrument, a stabilizable articulation actuator includes a rotationally stabilizable disk seated in a well, and a finger-operable lever configured to rotate a rotationally stabilizable disk to stable position. The finger-operable lever stabilizes the articulable joint in an articulated position by way of transferring force from the actuator through the force transfer cables to the articulable joint. In some embodiments, the stabilizable articulation actuator is mounted orthogonally or transverse to a central longitudinal axis of the instrument, as represented, for example, by the shaft. Thus, in these embodiments, the planes within the rotationally stabilizable disk and the finger operable lever rotate are orthogonal or transverse to the central longitudinal axis of the instrument. Typical embodiments of the finger-operable lever include two opposing arms, each arm of the lever being connected to a force transfer cable, the lever is configured such that its rotation moves a first transfer cable in a distal direction, thereby applying tension to the first transfer cable, and a second cable in a proximal direction, the second cable thereby being relieved of tension.

In some embodiments of the instrument, the rotationally stabilizable disk includes at least one spring portion biased circumferentially outwardly against a wall of the circular well, a circumferentially peripheral edge of the spring comprising one or more teeth, the wall of the circular well comprising one or more detents, the one or more teeth and the one or more detents configured to be mutually engageable. A rotational configuration in which teeth and detents are so engaged represents a stable position of the articulation actuator. In some embodiments, the rotationally stabilizable disk comprises two or more spring portions biased circumferentially outwardly against a wall of the circular well, the spring portions being distributed at equidistant intervals on the circumferential periphery. In some embodiments, the distribution of spring portions provides a circumferentially balanced distribution of forces impinging on the stabilizable disk. This balance of impinging centripetal forces advantageously supports a smooth rotation of the disc about its center.

In some embodiments, the rotationally stabilizable disk and the well in which it sits are adapted to stabilize rotation of the disk at any one position of a set of stable positions spaced apart at intervals within an arc of disk rotation. In some of these embodiments, the arc of rotation of the rotationally stabilizable disk encompasses about 90 degrees, including about 45 degrees in either direction from a neutral position wherein the finger operable lever is orthogonal to the shaft. The set of stable positions are typically spaced apart at regular intervals within the arc of rotation, such as set positions spaced apart at about 15 degrees. Typically, one of the stable positions is a neutral position, wherein the finger operable lever is orthogonal to the shaft. In general, articulating aspects of the articulable joint correspond to rotational aspects of the rotationally stabilizable disk. Thus, in some embodiments, the arc of articulation of the articulable joint substantially corresponds to the arc of rotation of the rotationally stabilizable disk. And, in some embodiments, the articulable joint is adapted to stabilize at a set of stable positions spaced apart at intervals that substantially correspond to the stable positions of the rotationally stabilizable disk.

In some embodiments, the rotationally stabilizable disk and the well in which it sits are configured such that the disk can be stabilized at a position by a level of resistance to rotation of the disk that can be overcome by application of torque to the finger operable lever. In another aspect, the rotationally stabilizable disk and the well in which it sits are configured such that rotation of the disk through a stable position requires applying a torque to the mechanism via the finger operable lever that is greater than the torque required to rotate the disk through portions of the arc between the stable angle positions. For example, the torque required to rotate the rotationally stabilizable disk with the finger operable lever through a stable position may be in the range of about 2 to about 10 lbs. And for example, the torque required to rotate the rotationally stabilizable disk with the finger operable lever through portions of the arc of rotation between the stable positions may be less than about 2 lbs.

In some of these embodiments of the instrument, the stabilizable articulation actuator may further include a cable tensioning mechanism proximal to the rotatable finger-operable lever. One example of a cable tensioning mechanism includes a spring plate as described further below and depicted herein. Embodiments of the spring plate include two opposing arms, one of the at least two force transfer cables is threaded through each arm of the rotatable finger-operable lever, through the spring plate, and then terminating proximal to the spring plate. As noted above, the force cables or cables move in opposite longitudinal directions as they drive articulating movement of the end effector, one moving distally and the other proximally. The spring plate is configured to maintain tension on the force transfer cable that is moved in a distal direction; absent the force provided by the spring, the distal-moving force cable could accumulate a problematic degree of slack. In some embodiments of the spring plate, each arm of the spring plate includes a circumferentially outward-facing open slot through which one of the force transfer cables is threaded. Further, each arm of the spring plate may include a circumferentially inward-facing open slot configured to engage a spring plate retention tab.

In some of these embodiments of the instrument, each arm of the finger operable lever includes a spring plate retention tab on a distal facing surface of the lever, and the spring plate comprises two opposing circumferentially inward facing slots. The tabs and the inward facing slots are configured to mutually engage in such a way so as to stabilize the spring plate against lateral slippage when the finger operable lever is in a rotated position.

In some embodiments, the articulation actuator is further configured to stabilize the end effector at a stable angle, the stable angle of the end effector being any one of a set of angles spaced apart at intervals within the arc of end effector articulation. In some embodiments of the electrosurgical instrument, the end effector is a set of forceps or jaws comprising a first jaw and a second jaw. The first and second jaw may also be referenced by terms such as an upper jaw and a lower jaw. Typically, the set of jaws includes a plurality of bipolar electrodes configured to receive energy from an energy source and to deliver the energy to the target site.

In some embodiments of the electrosurgical instrument, the articulable joint includes one or more pivotable links intervening between a distal end of the elongated shaft and a proximal end and the end effector. Some embodiments of the articulable joint include two or more interconnected pivotable links. The property of having, for example, one or more intervening pivotable links may also be understood as the articulable joint as whole having two or more intervertebral spaces within which pivoting may occur, or as the articulable joint as whole having two or more interconnected sites of pivoting articulation. In a typical configuration, interconnected links of the articulable joint, as well as the distal end of the shaft and the proximal end of the end effector, include ball-like or cylindrical projections engageable in complementary grooves.

In various embodiments, the articulable joint is configured to pivot the end effector within an arc of about 90 degrees, the arc including about 45 degrees in either direction from a neutral position. In general, the angle of articulation is considered to be the angle of a line tangent to the distal end of the articulable joint with respect to a line corresponding to the central longitudinal axis of the shaft. By virtue of the rotational stabilizing mechanism and by way of the operation of the force transfer cables, the articulable joint is stabilizable at a set of angles spaced apart at intervals within the arc of about 90 degrees. The set of angles that are spaced apart at intervals within the arc of rotation includes set angles spaced apart at about 15 degrees. Typically, one of the stabilized angles is a neutral angle, set at zero degrees with respect to the central longitudinal axis of the shaft. Finally, in some embodiments of the instrument, the articulable joint is adapted to be stabilizable at a desired angle of articulation.

Embodiments of the articulable joint and its distal connection with the end effector and its proximal connection to the shaft are configured such that various operational aspects of the end effector of the instrument are unaffected by the articulated position of the end effector. Thus, for example, the operation of opening and closing of the jaws, and the force that can be applied by through the jaws when closing, are both independent of the articulated position of the jaws. Similarly, movement of the blade occurs and all electrosurgical performance capabilities are unaffected by the articulated position of the jaws.

In some embodiments, an instrument with a set of jaws may further include a blade and a blade drive member collectively configured to be able to separate tissue at a target site into two portions when the tissue is being grasped by the set of jaws. The blade may be configured to reside in a home position distal to the articulable joint, and to be able to move distally within the set of jaws. The blade-driving member is typically disposed through the articulable joint, and operable through the joint in any position of articulation. The blade driving member may be configured as a push and pull mechanism; and an actuator configured to control the distal advancement of the blade and the proximal retreat for the blade may reside in the handle of the instrument.

Some embodiments of the electrosurgical instrument take a form that does not necessarily include a handle or a shaft; instead, for example, the jaws may be mounted on any suitable base. Embodiments such as these, could, for example, be incorporated into a robotic apparatus. These embodiments include a set of jaws associated with a base, the set of jaws enabled to deliver radiofrequency energy to a target site, an articulable joint positioned distal to the base, a stabilizable articulation actuator disposed in association with the base, an articulable joint positioned between the base and the set of jaws; and at least two force transfer cables for translating rotational movement of the articulation actuator into articulating movement of the set of jaws. In these embodiments, the articulable joint is configured to articulate the set of jaws angularly within an arc of articulation, and the articulable joint has least one pivotable link positioned between a distal end of the shaft and a proximal end of the set of jaws. In typical embodiments, the force transfer cables are operably connected at their proximal end to the articulation actuator, and operably connected at their distal end through the articulable joint to a proximal portion of the set of jaws. In some of these embodiments, the stabilizable articulation actuator is configured to stabilize the articulable joint at a stable angle by stabilizing the force transfer cables. The stable angle of the articulable joint may be any one of a set of angles spaced apart at intervals within the arc of joint articulation.

Embodiments of the provided technology also include a method of electrosurgical tissue sealing that includes moving a set of electrosurgical jaws into the proximity of a target tissue site. The jaws are positioned on a distal end of an articulable joint; the articulable joint is positioned distal to a shaft of an electrosurgical device. Embodiments of the method may include rotating a stabilizable articulation actuator with a finger operable lever. The method may further include articulating the jaw set with the articulable joint in order to position a distal end of the jaws into a desired angle or position of articulation such that when the jaws are closed they grasp the target tissue site. The method may then further include grasping the target tissue site with the jaws. The method may then further include delivering radiofrequency energy to the target tissue site from the jaws to seal the target tissue site. The method may still further include cutting through the newly sealed tissue site.

Embodiments of the method may include moving a set of jaws of an electrosurgical instrument into proximity of a target tissue site, the set of jaws being positioned on the instrument distal to an articulable joint. The method may further include rotating a stabilizable articulation actuator with a finger operable lever to a desired rotational position, and thereby articulating the articulable joint to a desired angle of articulation. The method may further include stabilizing the stabilizable articulation actuator in the desired rotational position, and thereby stabilizing the articulable joint in the desired angle of articulation.

The angular articulation of the articulable joint at an angle may be understood to refer to an angle associated with a line tangent to the distal end of the articulable joint with respect to the central longitudinal axis of the shaft of the instrument. Similarly, the angle of articulation associated with an end effector, such as a set of jaws, refers to an angle of a line associated with the common longitudinal axis of the jaws (as taken when the jaws are closed) with as compared to a line corresponding to the central longitudinal axis of a the shaft of the instrument. In general, a desired angle of articulation of either the articulable joint or an end effector distal to the joint refers to an angle such that the jaws are closed, they will close around and grasp the tissue targeted for electrosurgical engagement.

In some embodiments, rotating the stabilizable articulation actuator occurs by way of rotating a rotationally stabilizable disk, and, wherein stabilizing the stabilizable articulation actuator occurs by way of stabilizing a rotationally stabilizable disk.

Some embodiments of the method may further include articulating the set of jaws in accordance with rotating the stabilizable articulation actuator. And in some embodiments, the method may further include stabilizing the set of jaws in a desired angle of articulation in accordance with stabilizing the articulable joint in the desired angle of articulation.

Some embodiments of the method including rotating a finger-operable lever associated with the articulation actuator, thereby rotating the rotationally stabilizable disk within the actuator. Some of these embodiments may further include tensioning the force transfer cables with a tensioning mechanism associated with the finger-operable lever. The method may further include driving the movement of at least two force transfer cables in accordance with rotating the rotationally stabilizable disk. In such embodiments, driving the movement of the at least two force transfer cables includes applying tension from the proximal end of one of the force transfer cables and relieving tension from the other force transfer cable, the proximal ends of the force cables being operably engaged to the stabilizable articulation actuator.

In typical embodiments of the method, articulating either the articulable joint or the end effector refers to a capability of pivoting within an arc of about 45 degrees in either direction from a centerline within a plane, thereby providing a total pivotable range of about 90 degrees. In some embodiments of the instrument, the articulable joint includes one or more pivotable links positioned between a distal end of a shaft of the instrument and a proximal end of the jaws. In these embodiments, articulating the articulable joint may include pivoting the one or more pivotable links with respect to each other or with respect to the distal end of the shaft or the proximal end of the jaws.

Moving the set of jaws into proximity of a target tissue site may occur in several aspects, including a step of advancing the set of jaws the jaws through a trocar into a laparoscopic operating space, and a step of rotating the jaws. Rotation, in this context refers to rotating the jaws about their central common longitudinal axis, such axis defined by the jaws when they are in a closed position, or as represented by a common base portion of the jaws.

In some embodiments, rotating the set of jaws around their central longitudinal axis includes rotating from a neutral position within a range of up to about 180 degrees on either side of the neutral position. In various embodiments, wherein rotating the set of jaws around their central longitudinal axis of the set of jaws occurs by way of rotating a shaft of the electrosurgical instrument, which in turn, may occur by rotating a shaft rotating actuator of the instrument.

In various embodiments of the method, stabilizing the set of jaws in the desired angle of articulation is a step performed in conjunction with or simultaneously with articulating the articulable joint to its desired angle of articulation. Stabilizing the jaws at a particular angle of articulation, such as a desirable angle for grasping target tissue, may occur in close or causal relation to stabilizing the articulable joint, stabilizing force transfer members that control the angle of the articulable joint, and stabilizing a rotationally stabilizable disk with the stabilizable articulation actuator.

More particularly, stabilizing the stabilizable articulation actuator in the desired position may include engaging teeth on the periphery of a rotationally stabilizable disk with complementary detents on an inner aspect of a well in which the rotatable disc is housed. In another aspect, stabilizing the stabilizable articulation actuator may include rotating a lever of a stabilizable articulation actuator through a portion of an arc of relatively low rotational resistance until the lever encounters a position of relatively high rotational resistance, such position being a position of articulated stability. In yet another aspect, wherein stabilizing the stabilizable articulation actuator may include rotating a lever of a stabilizable actuator through a portion of an arc that may include one or more regions of moderate rotational resistance and one or more regions of high rotational resistance, until the lever encounters a particular position of high rotational resistance wherein the jaws are in a desired position of articulation. In the context of this latter embodiment, rotating the lever through a region a low rotational resistance may include applying a torque to the lever in the range of less than about 2 lb. inches, and rotating the lever through a region a high rotational resistance may include applying a torque to the lever in the range of about 2 to about 15 lb. inches.

Embodiments of the method may include further steps, such as grasping the target tissue with the set of jaws, and such as opening the set of jaws prior to the grasping step. The method may further specifically include delivering radiofrequency energy to the target tissue site after the jaws have grasped the target tissue site. Some embodiments of the method may include multiple electrosurgical treatments once the jaws have entered the laparoscopic operating space. As such, the method may further include moving the set of jaws to proximity of a second site while maintaining the set of jaws at the previous angle of articulation, and repeating the grasping step and the delivering energy step, these steps being directed toward the second target site.

In another aspect, the disclosed method of articulating and stabilizing an end effector of an electrosurgical instrument may be understood as a series of articulating steps that can be combined with a series of stabilizing steps to achieve articulation and stabilization of an end effector at a desired articulated angle. Accordingly, articulating the end effector may include rotating a finger operable lever, rotating a stabilizable rotatable disk, moving force transfer cables translationally, articulating an articulable joint, and articulating the end effector. Stabilizing the end effector may include stabilizing the stabilizable rotatable disk at a desired rotational position, stabilizing the finger operable lever at the desired rotational position, stabilizing the translation of force transfer cables at a desired translational position, stabilizing the articulable joint at a desired angle of articulation, and stabilizing the end effector at the desired angle of articulation. By embodiments of this method, rotating the finger operable lever may result in rotating the stabilizable disk through one or more regions of relatively low rotational resistance and relatively high rotational resistance. Further by this method, stabilizing the end effector may include stopping rotation of the stabilizable disk at a position of relatively high rotational resistance.

DETAILED DESCRIPTION OF THE INVENTION

Figure 1:
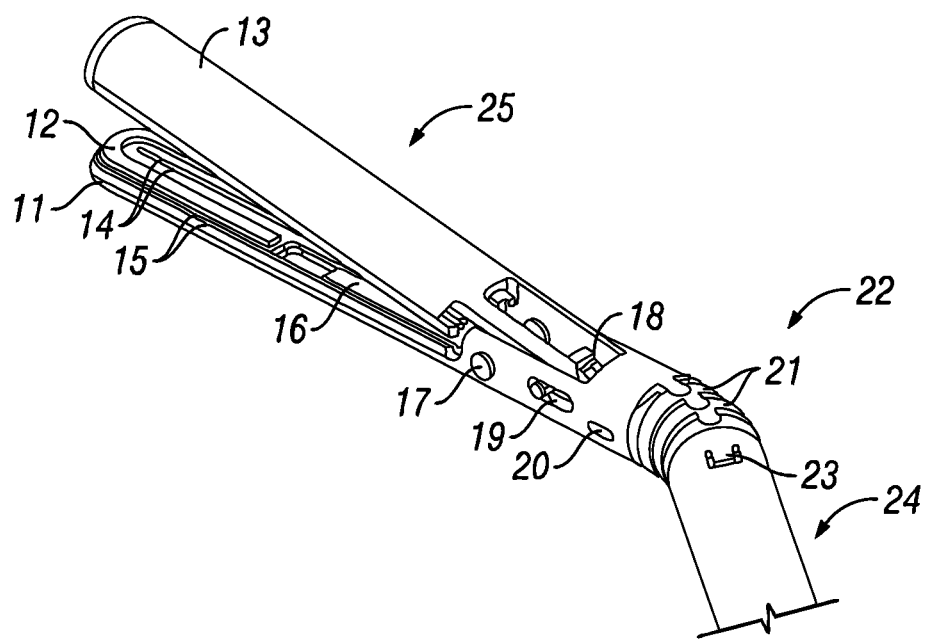
FIG. 1 is a perspective diagram showing an articulable joint of an articulable electrosurgical instrument.

Aspects of the technology provided herein include a method and apparatus for articulating the joint of an articulable electrosurgical instrument that would typically used in a laparoscopic environment, but is also suitable for use in an open operating environment. Examples of electrosurgical devices that could incorporate the articulable features as described herein, include devices as described in the following, all of which are incorporated herein, in their entirety: U.S. Pat. No. 7,862,565 entitled "METHOD FOR TISSUE CAUTERIZATION" issued on Jan. 4, 2011; U.S. Pat. No. 7,803,156 entitled "METHOD AND APPARATUS FOR SURGICAL ELECTROCAUTERY" issued on Sep. 28, 2010; U.S. Pat. No. 7,794,461 entitled "METHOD AND APPARATUS FOR SURGICAL ELECTROCAUTERY" issued on Sep. 14, 2010; U.S. application Ser. No. 11/743,579 entitled "SURGICAL TOOL" filed on May 2, 2007, published on Jul. 17, 2008 as U.S. Publication No. 2008/0172052A1; U.S. application Ser. No. 11/382,652 entitled "APPARATUS FOR TISSUE CAUTERIZATION" filed on May 10, 2006, published on Nov. 16, 2006 as U.S. Publication No. 2006/0259034A1; U.S. application Ser. No. 11/671,891 entitled "ELECTROCAUTERY METHOD AND APPARATUS" filed on Feb. 6, 2007, published on Jun. 7, 2007 as U.S. Publication No. 2007/0129726A1; U.S. application Ser. No. 12/121,734 entitled "ELECTROCAUTERY METHOD AND APPARATUS" filed on May 15, 2008, published on Sep. 11, 2008 as U.S. Publication No. 2008/0221565A1; U.S. application Ser. No. 12/062,516 entitled "ELECTROCAUTERY METHOD AND APPARATUS" filed on Apr. 4, 2008, published on Sep. 18, 2008 as U.S. Publication No. 2008/0228179A1; U.S. application Ser. No. 12/410,322 entitled "ELECTROCAUTERY METHOD AND APPARATUS" filed on Mar. 24, 2009, published on Jul. 16, 2009 as U.S. Publication No. 2009/0182323A1; U.S. application Ser. No. 11/671,911 entitled "ELECTROCAUTERY METHOD AND APPARATUS" filed on Feb. 6, 2007, published on Aug. 9, 2007 as U.S. Publication No. 2007/0185482A1; U.S. application Ser. No. 12/748,229 entitled "IMPEDANCE MEDIATED POWER DELIVERY FOR ELECTROSURGERY" filed on Mar. 26, 2010, and U.S. application Ser. No. 12/907,646 entitled "IMPEDANCE MEDIATED CONTROL OF POWER DELIVERY FOR ELECTROSURGERY" filed on Oct. 19, 2010.

The presently described medical instrument, a bipolar electrosurgical device by way of example, may be configured to seal tissue and/or to cut tissue, and has an end effector that can be articulated through the operation of an articulable joint. Embodiments of the instrument typically have a set of opposing jaws that can be articulated up to an angle of about 45 degrees, both to the left and the right from a centerline defined by the central longitudinal axis of the shaft of the instrument, for a total articulation range of about 90 degrees. Aspects of the technology also provide a proper bend radius and support for a jaw actuation member and a cutter-driving member. In some embodiments, a bendable support for the drive includes tightly wound coil springs.

Some embodiments of the technology further include a mechanism and a method to control the degree of articulation with an actuator disposed at the handle of the articulable electrosurgical instrument. Embodiments of the technology may further include a locking mechanism, or more generally, a stabilizable articulation actuator, to prevent motion of the articulable joint while an operator, typically a surgeon, performs electrosurgical procedures with the device. Embodiments of the locking mechanism also include an indexing feature with which a surgeon operator can index and choose the necessary amount of angle between preset angles.

Some embodiments of the technology include, in the form of a distally positioned articulable joint or wrist, a set of pivotal vertebra, links, hinges, or flexible elements that are interconnected by pins, or by a snap fit, or by tension applied by a force transfer member. Each vertebra is adapted to pivot in relation to the longitudinal axis of the shaft and jaw set, thus allowing left and right articulation. The angle of articulation is controlled by connecting or force-transfer members, such as wires or cables, which are disposed along both sides of the articulable joint. The connecting wires are proximally routed up the shaft and connected with tension to a control mechanism at a device handle, and function by transferring force from the handle to the joint.

Embodiments of the links or vertebrae collectively form a proper bend radius in embodiments of the distal articulable joint, a bend radius that is sufficiently large that it allows for a force transfer wire or cable to pass through the joint without kinking. Further, in some embodiments, a tightly wound coil spring is housed within the joint to route the wire. The tightly wound coil spring provides additional support to the wire, such that when the wire is moved back and forth, proximally or distally, it does not buckle or kink.

Embodiments of the control mechanism at the handle include an indexing disk and finger operable lever that receives the force transfer cables or wires from the joint. The indexing disk is pivotally mounted at the handle of the instrument, and the shape of the control mechanism allows for concentric rotation about the pivot so that the length-wise motion of the wires or cables along the shaft can be controlled, based upon the distance from the pivot to the attachment point of the wires or cables. The distances that the force transfer cables move controls the articulation position or angle; these distances are available as preset options according to the geometry of the joint and the indexing disk and its lever.

Figure 6:
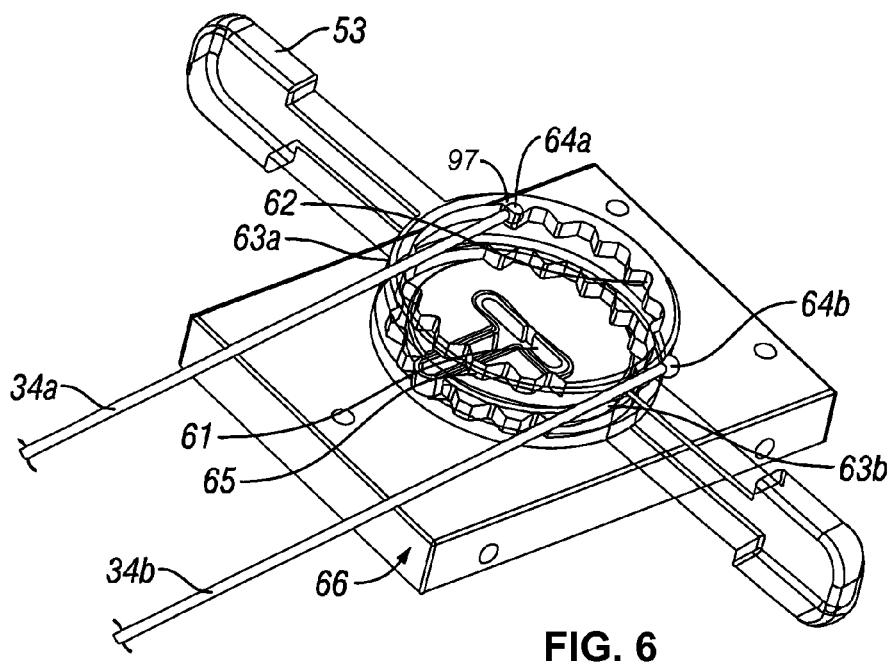
FIG. 6 is a perspective schematic view of an indexing mechanism for an articulable electrosurgical instrument.
Figure 7:
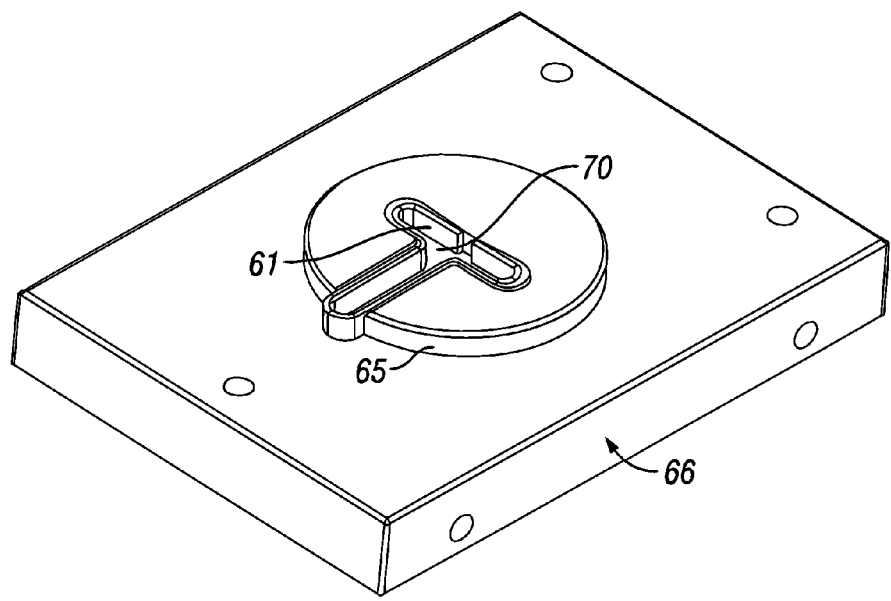
FIG. 7 is a perspective schematic view of a detent mechanism for an articulable electrosurgical instrument.
Figure 8:
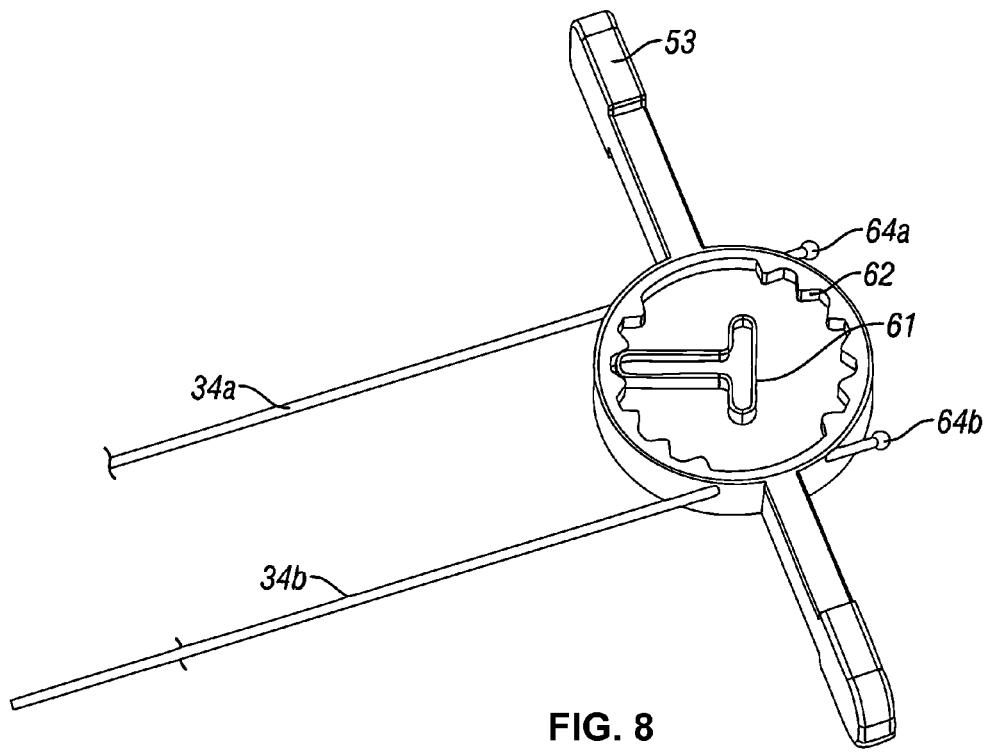
FIG. 8 is a perspective schematic view of a detent and indexing mechanism for an articulable electrosurgical instrument.

Several embodiments of the technology have a stabilizable articulation actuator include indexing or locking features. This mechanism, in its various embodiments can specify particular angles of articulation, and can stabilize the end effector distal to the joint at particular angles. The stabilized or lockable angles are located at spaced apart intervals within the arc of articulating rotation. In a first embodiment, a spring steel member is formed into a geometry that deflects when a force is applied, as with a leaf spring. An example of this embodiment, with a spring steel member is shown in FIG. 6; other aspects of the locking and indexing mechanism are shown in FIGS. 7 and 8. The leaf spring is housed within a circular carrier, with only the deflectable portion of the spring accessible and protruding from a circular carrier. A rotating member with a circular portion removed from its pivot area fits over the circular carrier. A tooth pattern is also removed from along the inner diameter of the circular portion of the rotating member. The rotating member includes arms extending from its center body to which the cable or wires are attached. The leaf-like spring protrudes into the indentations created by the tooth pattern. The distance between the teeth and the distance from the attachment point of the cable or wires to the pivot point control the articulation angle.

Figure 9:
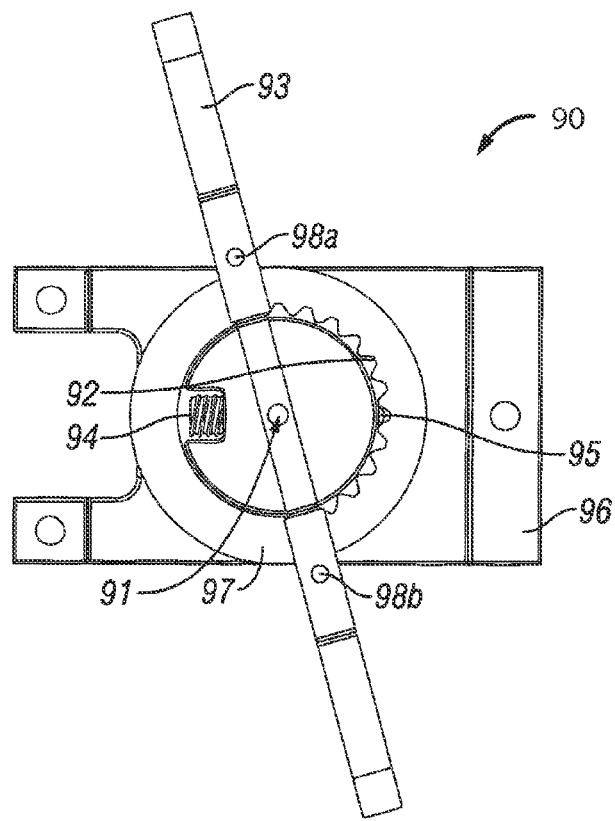
FIG. 9 is a plan schematic view of a step ball detent mechanism for an articulable electrosurgical instrument.
Figure 10:
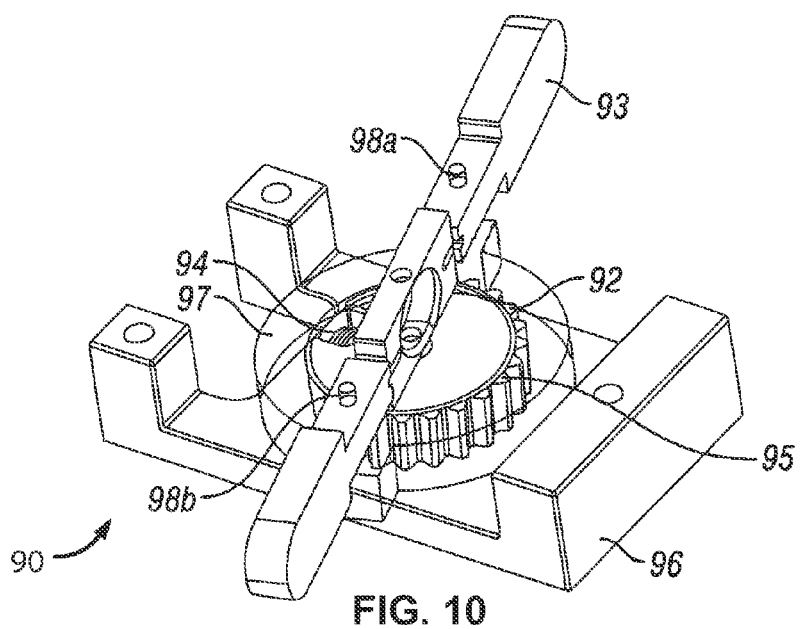
FIG. 10 is a perspective schematic view of the step ball detent mechanism for an articulable electrosurgical instrument.

In a second embodiment of a stabilizable articulation actuator with indexing or locking features, a spring plunger is mounted within a circular carrier opposite a step ball. The spring plunger mates with the indents created by the tooth pattern. Examples of this particular embodiment of a stabilizable articulation actuator are shown in FIGS. 9 and 10.

In a third embodiment of a stabilizable articulation actuator with indexing or locking features, the rotating member described above does not have arms extending from its center body. A wing is mounted on top of the rotating member. The wing is then manipulated to control the rotation around the circular carrier.

In a fourth embodiment of a stabilizable articulation actuator with indexing or locking features, a flexible plastic hinge, also known as a living hinge, is mounted near the handle. The living plastic hinge uses a V-shape that fits within a slot of an external housing that surrounds the living hinge. The tip of the V-shape protrudes from each slot. There is a series of slots along the length of the external housing. The housing engages with the cable and wires that control articulation of the joint. The operator can adjust and lock the joint articulation by first pressing down on the living hinge to disengage the current locked position, then moving the external housing from a proximal to a distal position or vice versa, which then locks by re-engaging with the living hinge at any various predetermined distances set by the slots. These distances determine the angle at which the joint is articulated.

Figure 12:
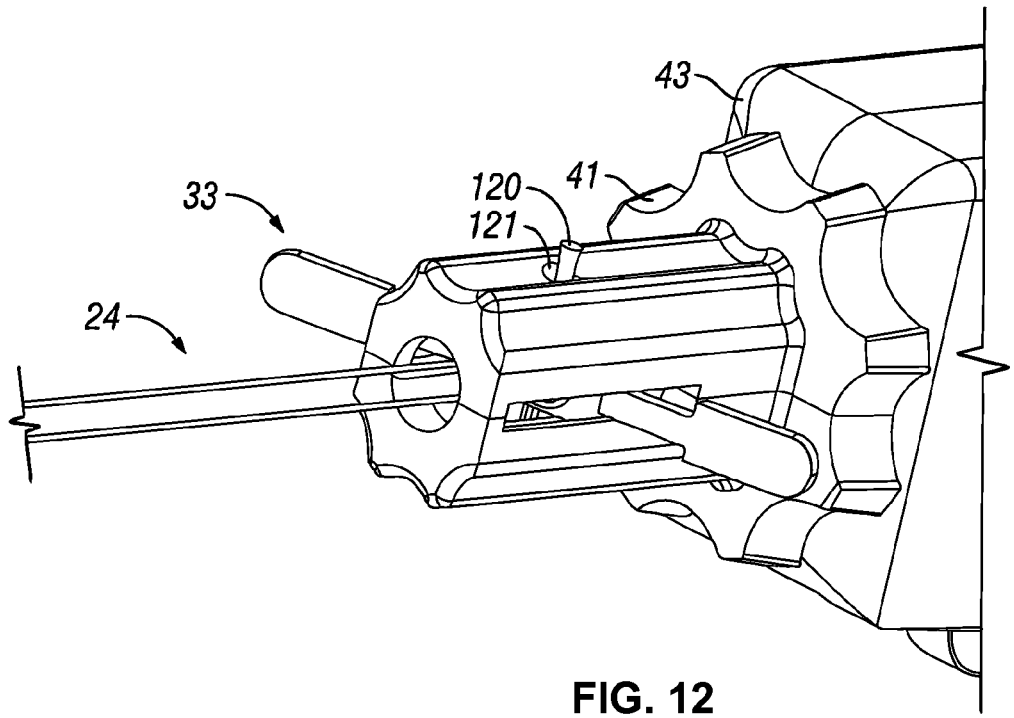
FIG. 12 is a perspective schematic view of a push lock mechanism for an articulation control in an articulable electrosurgical instrument.
Figure 13:
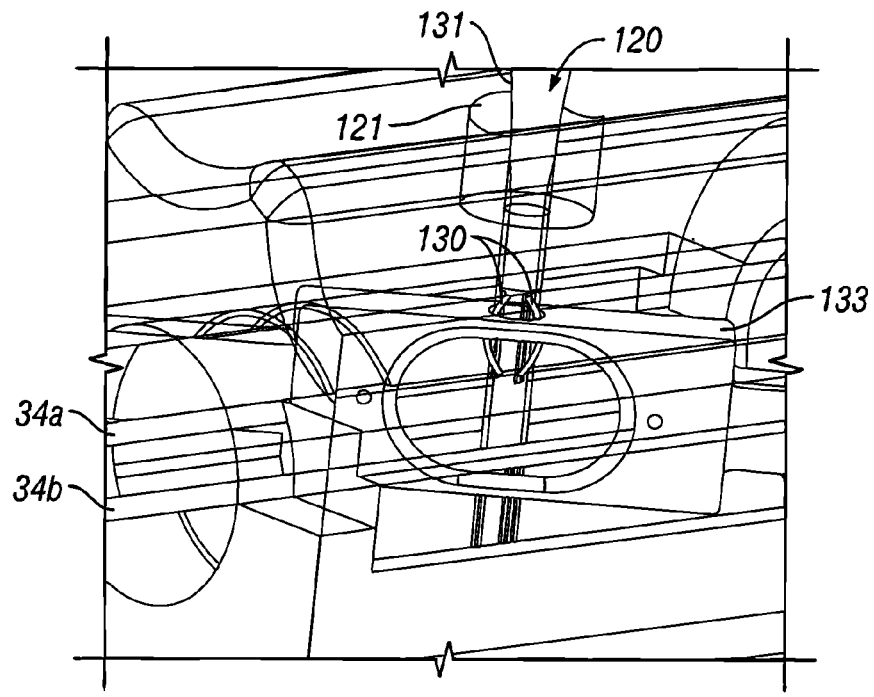
FIG. 13 is a phantom perspective schematic view of the push lock mechanism for an articulation control mechanism in an articulable electrosurgical instrument.
Figure 14:
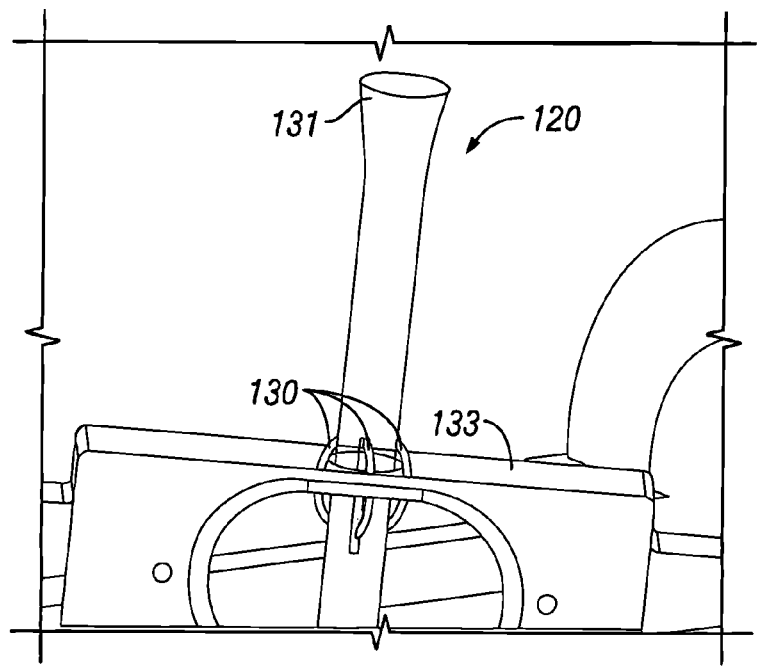
FIG. 14 is a perspective schematic view of a grab knob for the push lock mechanism in an articulation control for an articulable electrosurgical instrument.

In a fifth embodiment of a stabilizable articulation actuator with indexing or locking features, the rotating mechanism described above rotates freely around the pivot. When an operator or surgeon has determined the angle of articulation, an indexing pin mounted on top of the pivot is depressed, which locks the joint angle and the rotating mechanism, thus preventing any further movement of both the rotating mechanism and joint. This can be accomplished using a wedge-like design that is anchored within the pivot pin, which in this embodiment is a tube. A minimum of a single slot is designed into the pivot pin. When the button is depressed, the inherent spring properties of the button flare from the slot. The flaring material uses friction to prevent movement of the rotating mechanism. The button itself remains in place due to a wedge design at the top. An example of this particular embodiment of a locking and indexing mechanism is shown in FIGS. 12, 13, and 14, as described further below.

In a sixth embodiment of the disclosed technology, a stabilizable articulation actuator of the electrosurgical instrument includes an indexing or rotational position stabilizing disk with spring piece arms that have teeth that can engage complementary detents in a receptacle or well within which the disk is rotatably seated. This particular embodiment of an articulation actuator includes a non-locking mechanism. Articulation angles of an articulation joint are not locked into place, but are, instead stabilized by a relatively high level of rotational resistance in the actuator that can nevertheless be overridden by a level of torque easily applied to a finger operable lever. Examples and views of this sixth embodiment are shown in FIGS. 17-28, and described further below.

In the description of the disclosed technology and as shown in FIGS. 1-28, embodiments of the stabilizable articulation actuator may be included within or in association with a shaft rotator portion of an electrosurgical instrument for design considerations. However, in other embodiments of the disclosed technology, these two functional actuators could be positioned in physically separate locations. Further, other embodiments of the disclosed technology, including a stabilizable articulation actuator and an operably connected articulable joint, may be included in a broad range of devices, such as those that do not deliver radiofrequency energy, or in devices that do not have a shaft, that do not have a handle, or which have neither a shaft nor a handle.

Further to the foregoing description, a more detailed explanation is now provided in connection with examples of the technology as depicted FIGS. 1-28. Many electrosurgical features of embodiments of the device, such as bipolar electrode pairs, are not shown in order to focus on features that provide articulability to the device. Details of electrosurgical features may be found in the patent applications identified above.

FIG. 1 is a perspective view of a distal portion of an embodiment of an articulable electrosurgical device according to aspects of the technology; it shows a distal portion of the main shaft 24 of the electrosurgical device and an end effector, in this example, a jaw assembly 25 which includes lower jaw 11 and an upper jaw 13. In a more general aspect, jaw assembly may be described as having a having a first jaw 11 and a second jaw 13. Inasmuch as some embodiments of the device have a rotatable shaft and thus, a rotatable set of jaws, the terms upper and lower may have no absolute significance, but they may be useful in describing the jaws as they appear in figures, or as they may be so designated by marking or by convention. In this embodiment, the upper jaw is pivotable away from and toward the lower jaw about a pivot point 17, which typically includes a pin or axle. In other embodiments of the technology, the lower jaw may be pivotable as well, but in this particular embodiment, the lower jaw is fixed. Pivoting of the upper jaw is accomplished by transmitting tension to a jaw activation pin 18, which is moveable in an activation slot 19. Typically, tension is applied via a cable attached to the jaw activation pin. In this example of an end effector, the jaw set or assembly 25 is configured for such laparoscopic procedures as electrosurgical tissue sealing and cutting. Accordingly, as shown in the bottom jaw 11, a distal electrode 12 is provided, embedded in the plastic carrier 15. A second, proximal electrode 16 is also shown. A cutting groove 14 is shown for receiving a blade (not visible) during a tissue separating procedure that occurs in conjunction with tissue sealing. Also visible in FIG. 1 and FIG. 2 is an articulable wrist or joint 22, as described further below.

During laparoscopic electrosurgical procedures, it is desirable to be able to position the jaws of the device from left to right within an arc of a plane of articulating freedom to achieve the best angle of approach to a target tissue site; this capability is provided by an articulable joint or joints 22 that includes one or more articulation disks, links, or vertebrae 21. In this particular embodiment of articulable joint 22, two pivotable links 21 are shown intervening between the distal end of shaft 24 and the proximal end of jaw assembly 25. Articulation is accomplished by tensioning a pair of cables (described further below) that terminate distally where they are soldered or crimped in a groove at a cable termination point 20. FIG. 1 further shows a clamping slot 23, which functions as a lock for an outside shaft tube or clamping mechanism to hold the articulable joint 22 to the tube.

Figure 2A:
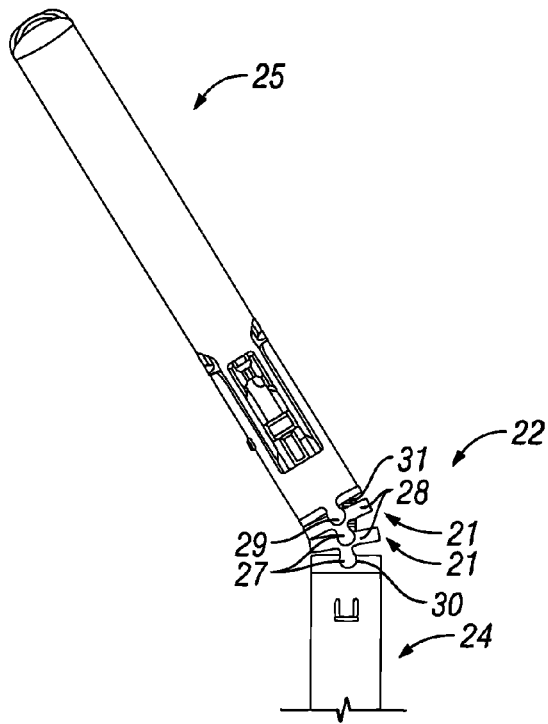
FIG. 2A is a plan view showing an articulable joint of an articulable electrosurgical instrument.
Figure 2B:
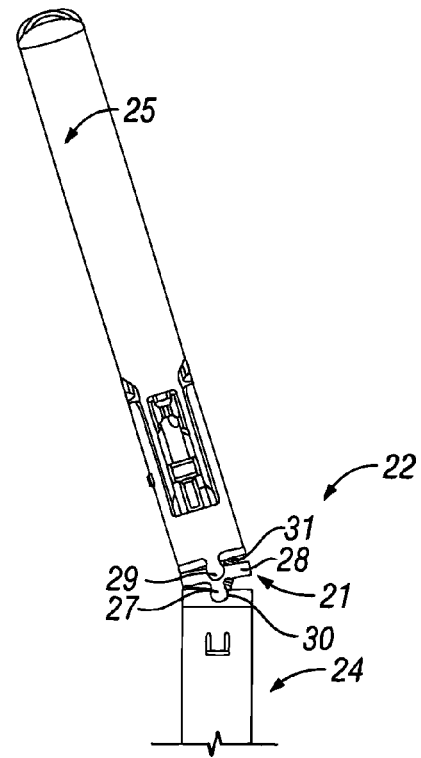
FIG. 2B is a plan view showing an articulable joint of an articulable electrosurgical instrument wherein an articulable joint comprises one link intervening between the shaft and the jaws.

FIG. 2A is a top or plan view of a distal portion of an embodiment of an articulable electrosurgical device showing the jaws 25 and shaft 24 disposed on opposite ends of an articulable joint 22. FIG. 2B is a plan view showing an articulable joint of an articulable electrosurgical instrument wherein an articulable joint comprises one link intervening between the shaft and the jaws. Embodiments of the articulable joint include interconnected pivotable, hinged links or disks; the disks 21 are articulated with one another and include a series of ball-like or cylindrical-like projections 27 that are engaged in complementary grooves 28. The jaw assembly 25 of this embodiment shows a particular distal-most, proximally directed ball-like projection 29 associated with the jaw assembly 25 that is engaged in a groove of an articulation link, and the shaft 24 includes a distal-opening complementary groove 30 for receiving a ball-like or cylindrically-shaped projection of an articulating disk. In some embodiments, the articulation range of the articulable joint is contained within an arc of a plane, although a proximally disposed shaft rotator can rotate the end effector, as a whole. Some embodiments of the articulable joint are stabilizable at a desired angle of articulation, thereby also stabilizing the end effector at a desired angle of articulation. A short segment of a cable 31 is shown in FIGS. 2A and 2B as well; the cable includes a coiled pipe sheath assembly and is used to operate a slidable blade within the jaw. As noted above, the coiled assembly allows the cable to bend with the articulation of the device without kinking.

Figure 15:
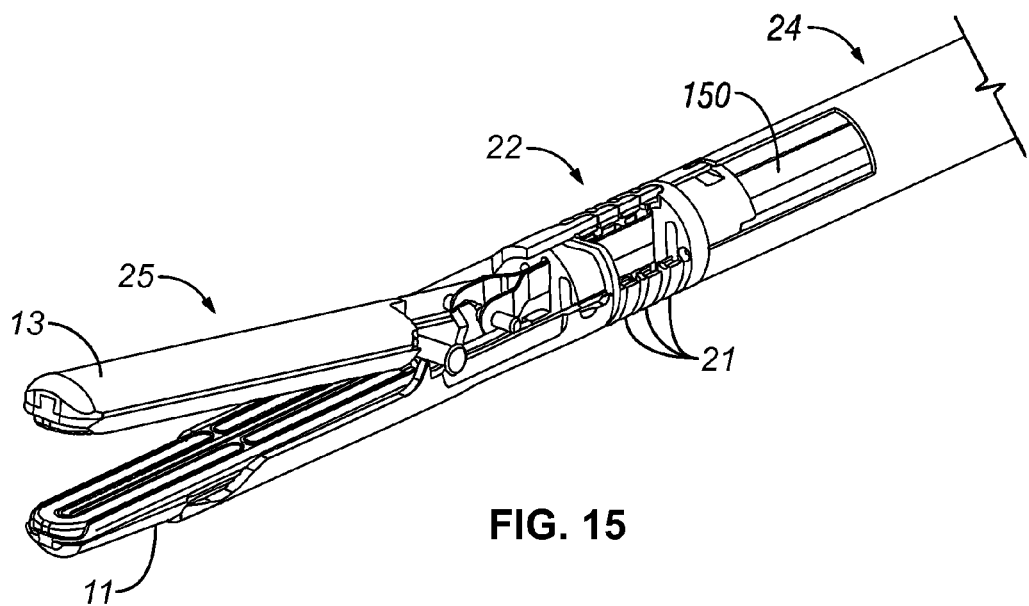
FIG. 15 is a perspective, partially cutaway view of an articulable electrosurgical instrument, showing a drive member.
Figure 17:
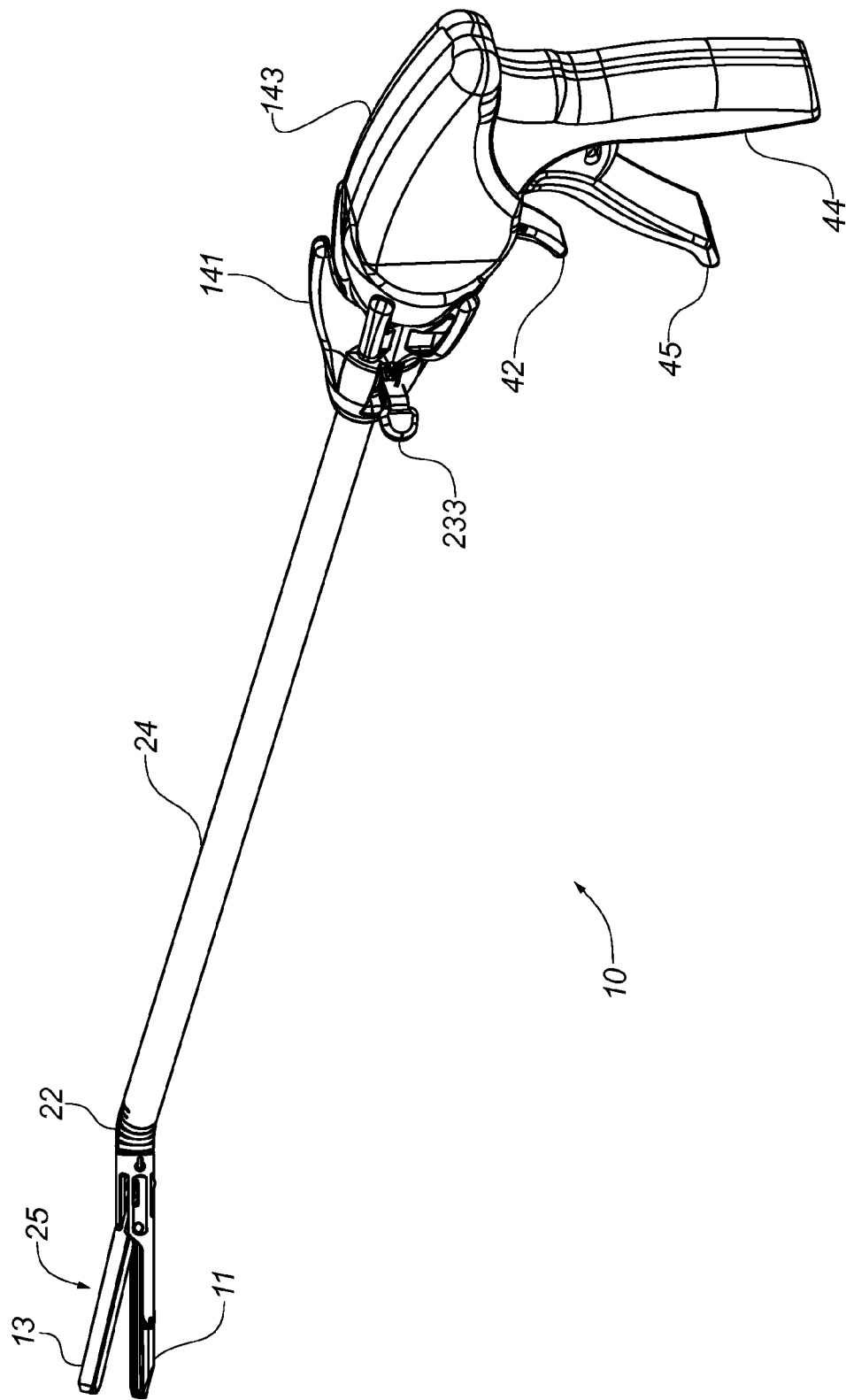
FIG. 17 is a perspective view of an embodiment of an articulable electrosurgical device, with an indexing mechanism proximal to the shaft, and an articulable joint positioned distal to the shaft and proximal to a set of jaws, the articulable joint in an articulating position. Other views of aspects of this embodiment are shown in FIGS. 18-28.

Embodiments of an articulable joint as provided herein include one or more pivotable links intervening between the distal end of the shaft and the proximal end of the end effector. An advantage associated with a plurality of links, e.g., two or more intervening articulable links, is that the plurality may provide an enhanced articulation angle range, and enhanced resolution and stability of articulated angles. An advantage of relatively few intervening links, such as one link, relates to ease of manufacturing assembly and lower cost. Examples of articulable joints that include one intervening link are shown in FIG. 2B. Examples of articulable joints that include two intervening links are shown in FIGS. 1 and 2A. An example of an articulable joint that includes three links is shown in FIG. 15. An example of an articulable that joint includes four links is shown in FIG. 17. Embodiments of an articulating links such as these described and depicted are but an example of an appropriate link configuration; other suitable link configurations are known in the art and may be included as embodiments of the technology.

Figure 3:
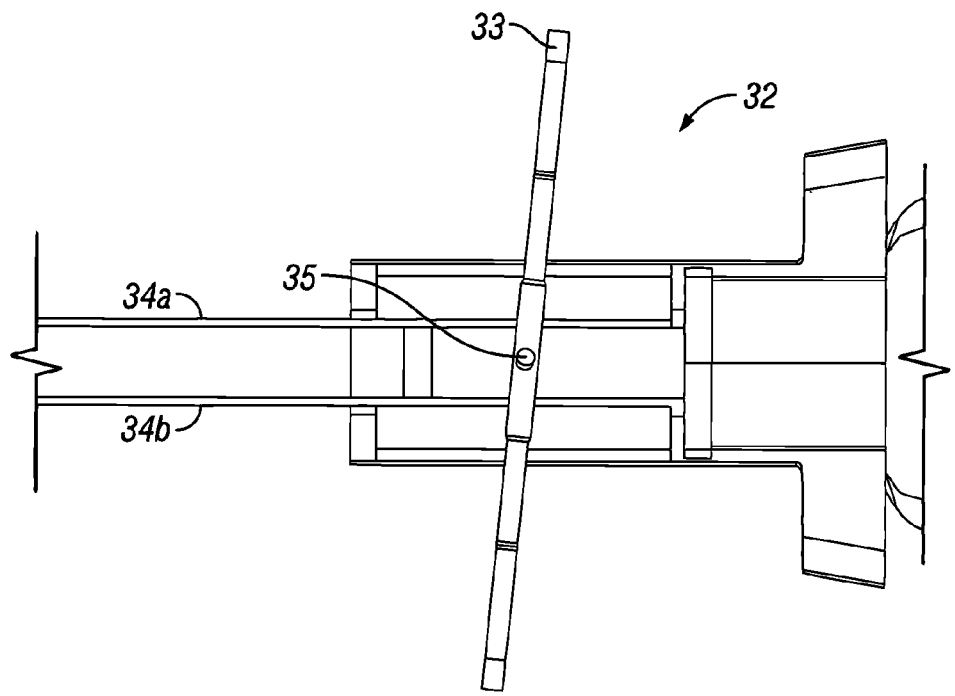
FIG. 3 is a schematic view showing a top cutaway of a joint articulation control mechanism of an articulable electrosurgical instrument.

FIG. 3 is a partially cutaway side schematic view of an embodiment of an articulation control or actuation mechanism 32 for operating the articulation joint. A joint articulation control member or lever 33 is shown having two finger surfaces at opposite ends of the control member; these finger surfaces allow a surgeon to pivot the control member about a pivot point 35. Parallel pretensioned control cables 34a/34b (comprising Nitinol or other suitable cable materials) are attached to respective points on the control member. This pivoting action of control member 33 respectively applies tension to and draws tension from the pair of control cables 34a/34b. Operation of the joint articulation control causes one cable of the paired cables to pull back on the jaw assembly 25 while the other cable releases tension, thus causing the jaw assembly to move left or right, as desired.

Figure 4:
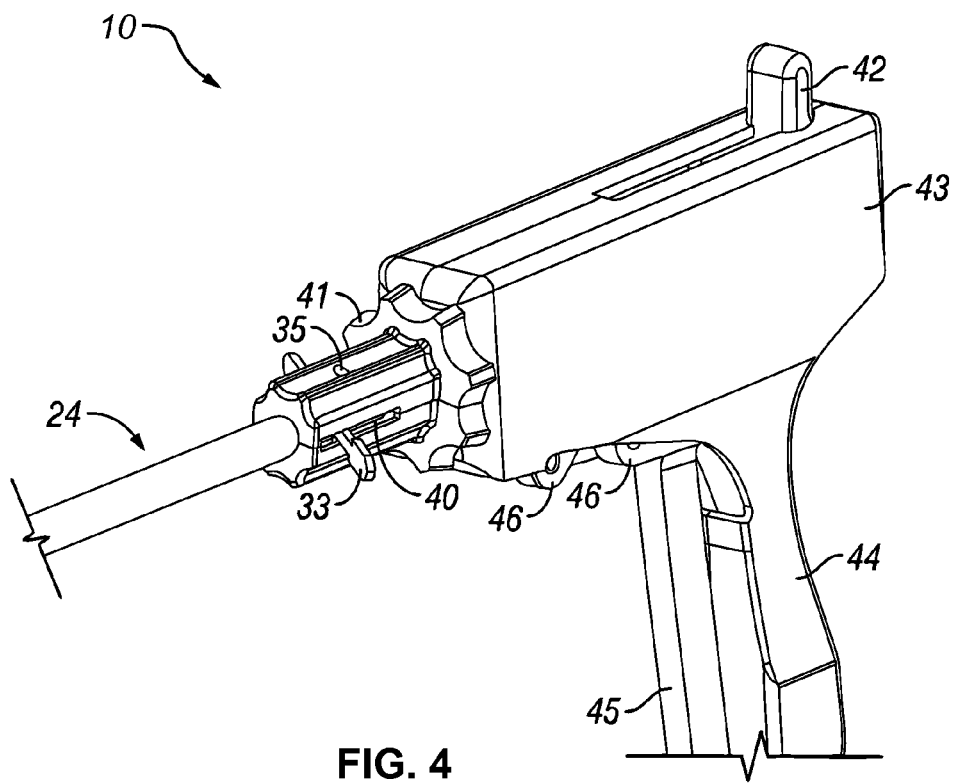
FIG. 4 is a perspective schematic view showing an articulable electrosurgical instrument.

FIG. 4 is a perspective view of a proximal portion of an articulable electrosurgical device 10 according to aspects of the technology showing a housing 43 having a handle 44 and a jaw activation trigger 45 that operates a four-bar linkage or other type of linkage 46 to transmit tension through the main shaft 24 and thereby operate the jaws to open and close them as desired. A blade actuator member 42 is also shown, by which a blade may be drawn through a cutting groove 14 (shown in FIG. 1). A shaft rotator or end-effector rotational actuator 41 allows the shaft to be rotated about a shaft access, while the joint articulation control member 33 allows the joint mechanism to be operated. Note in FIG. 4 that the joint articulation control mechanism 32 includes a control slot 40 that both guides and limits the travel of the joint articulation control member 33.

Figure 5:
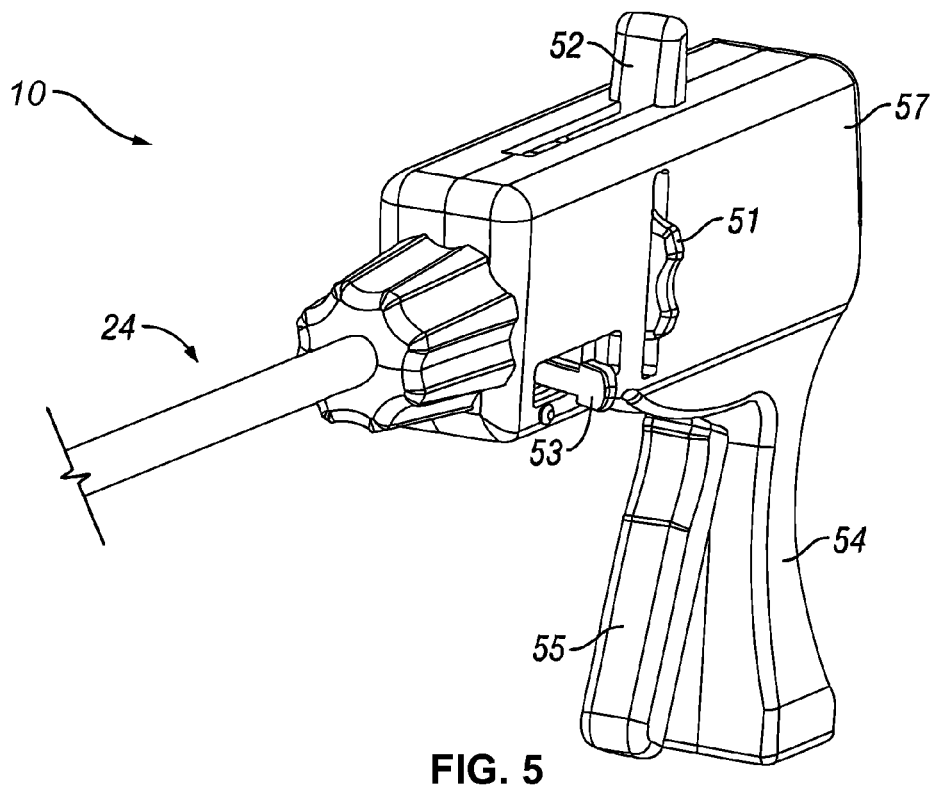
FIG. 5 is another perspective view of an articulable electrosurgical instrument.

FIG. 5 is a perspective view of a proximal portion of an embodiment of the articulable electrosurgical device 10 in which a shaft rotator 51 is contained within a housing 57. This embodiment also includes a blade actuator 52, a joint articulation control member 53, a handle 54, and a jaw activation trigger 55.

FIG. 6 is a perspective schematic view of an embodiment of a joint actuation control mechanism of the articulable electrosurgical device shown in FIG. 5; this embodiment of the control mechanism includes an indexing capability. A base portion 66 of indexing the indexing articulation control mechanism supports a ring projection 65 that, in turn, accommodates the control member 53. Tensioned cables 34a/34b each have termination balls 64a/64b that serve as cable stops. Cables 34a/34b are threaded through the control actuator member 53 by way of respective grooves 63a/63b. An indexing disk 97 includes a plurality of detents 62. A flat spring 61 is arranged to engage within the detents to provide a stop mechanism to secure the jaws in a selected position by preventing movement of the articulation control member 53, except when desired by an operator of the device.

FIGS. 7 and 8 provide detailed views of various features of the indexing articulation actuation mechanism shown in FIG. 6. FIG. 7 is a perspective schematic view of the base portion 66 of the articulation control mechanism that shows a spring mechanism 61 sitting in a recess 70 of the ring-like projection 65. FIG. 8 is a schematic perspective view of the articulation control member 53 showing the detents 62 in greater detail.

FIG. 9 provides a top view of an alternative embodiment of an indexing articulation control or actuation mechanism 90 for an articulable joint. A base portion 96 supports an articulation control member 93 that includes a plurality of detents 92 formed in a detent-indexing disk 97. The control member and detent-indexing disk are rotatably mounted on a base structure 96. Operation of control member 93 causes rotation of indexing disk 97 about a pivot point 91, and consequent engagement of a step ball 95 into one of a plurality of detents 92 within the indexing ring. A ball plunger mechanism 94 circumferentially opposite the step ball 95 maintains bias on the step ball. The indexing control member 93 includes a pair of proximal attachment points 98a/98b for control cables that extend distally to an articulable joint or wrist.

Figure 11:
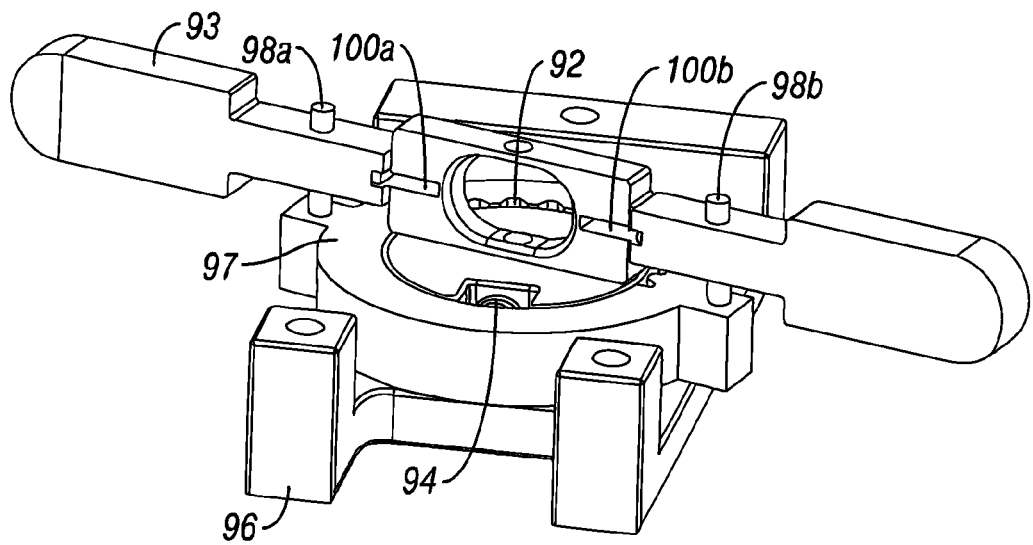
FIG. 11 is a second perspective schematic view of the step ball detent mechanism for an articulable electrosurgical instrument.

FIG. 10 is a perspective view of the index control mechanism for an embodiment of an articulation actuation mechanism 90 (as seen in top view in FIG. 9). FIG. 11 is a more horizontally oriented perspective view of the control mechanism for the articulation joint in an articulable electrosurgical device according to aspects of the technology. The arrangement of the articulation control member 93 in connection with the indexing ring 97 is shown, and in particular shows the attachment there between a pair of pins 98a/98b. FIG. 11 also shows a pair of grooves 100a/100b for receiving control cables (cables not shown in this view).

FIGS. 12-14 show a further embodiment of an indexing articulation actuation mechanism that includes an indexing pin. FIG. 12 shows an indexing pin 120 that is engaged in a slot 121. FIG. 13 is a cutaway perspective phantom view showing the indexing pin 120 comprising a head portion 131 and a plurality of flared portions 130 which engage or disengage with a locking block 133. Accordingly, this embodiment of the technology includes a jam lock in which depression of the pin 120 jams the flared portion of the pin 130 into the block 133 and thus prevents rotation of the actuation control mechanism. FIG. 14 is a detailed view of the jam mechanism showing the pin 120, head 131, and flares 130 in greater detail.

Figure 16:
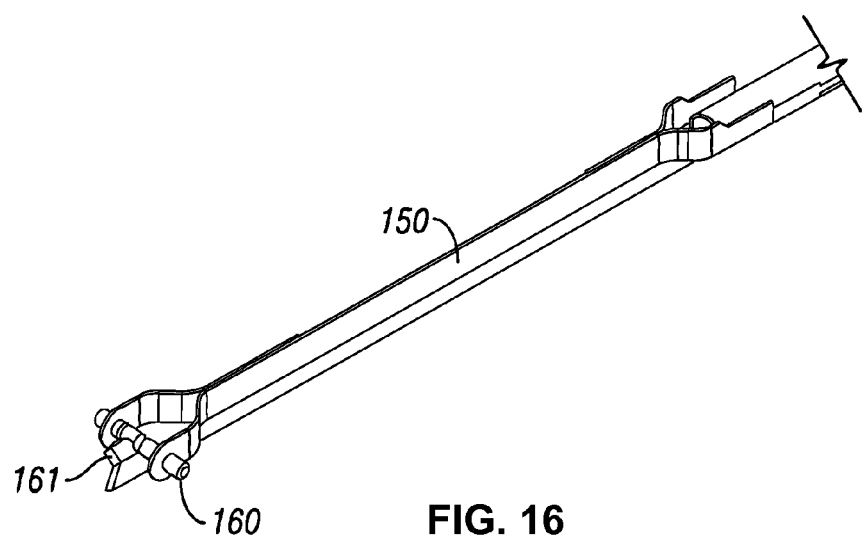
FIG. 16 is a perspective view of a drive assembly for a blade within an articulable electrosurgical device.

FIGS. 15 and 16 depict aspects of an end effector drive member of embodiments of an articulable electrosurgical device. An end effector drive member, in general, drives a particular function associated with the end effector. In this embodiment of an electrosurgical device, the end effector is a set of jaws, and accordingly, a drive member may control the opening and closing of the jaws. FIG. 15 is a perspective, partially cutaway view of a distal end effector portion of an articulable electrosurgical device, showing a drive member according to aspects of the technology. FIG. 15 shows the articulable joint 22 of the device, while FIG. 16 shows a jaw-activating band 150, a closing pin 160, and cutting blade 161, a distal portion of which extends back to the handle of the instrument, where an actuator that advances and retreats the blade resides. The operation of a drive member 150 that controls opening and closing of the jaws and the operation of the blade by distally advancing and retreating are performed by separate mechanisms, which operate independently.

The drive members may be made of a round wire (stainless steel or Nitinol), using tightly wound coil springs for support. The drive members may also be flat stainless steel bands 150, as shown in FIGS. 15 and 16. Instead of the round wire that serves as a drive member in some embodiments, this embodiment may include flat bands, and may support the bands with aspects of the internal structure of the links. Other embodiments may use flat polymer bands to provide additional support. These bands may be formed from polymers such as polytetrafluoroethylene (PTFE, Teflon™) or fluorinated ethylene propylene (FEP). The support structure may also include PTFE or FEP shrink tubing over the blade and/or the jaw actuation band.

An embodiment of an articulable joint 22 is also shown in FIG. 15. In this particular embodiment of articulable joint 22, three pivotable links 21 are shown intervening between the distal end of shaft 24 and the proximal end of jaw assembly 25.

FIGS. 17-28 provide views of a particular embodiment of an articulable electrosurgical device with a stabilizable articulation actuator and associated methods for its use, in accordance with the sixth embodiment of the technology as noted above. In some of these embodiments, the stabilizable articulation actuator is a substantially non-locking mechanism in that rotational angles are stabilized by virtue of the relative high resistance to rotation required to move the mechanism out of the stable angle position, in contrast to the relatively low resistance encountered during rotation of the mechanism between the angles that represent stable positions. In another aspect, it may be understood that moving through the regions of relatively high rotational resistance is part of the normal procedure by which a desired angle of articulation is arrived at. Embodiments of the stabilizable articulation actuator cooperate with the end effector, via cables, in order to control and stabilize the articulation angle of the end effector. Further details of the stabilizable articulation actuator are provided in the context of describing FIG. 20, below.

The stabilizable articulation actuator includes a cable tensioning mechanism 170 associated with the cross bar of a finger-operable lever that enhances the articulating performance of the distal articulable joint. The cable tensioning mechanism maintains a tension on cables 34a/34b, and allows greater tolerance in dimensions or manufacturing specification ranges of both proximal and distal elements of the articulable mechanism, as well as the length of cables, and further serves generally to retain or stabilize these elements in a functional configuration. In some embodiments, the cable tensioning mechanism 170 may comprise a spring plate, as shown in FIGS. 19-21, 23, and 25-27.

FIG. 17 is a perspective view of an embodiment of an articulable electrosurgical device 10, with a stabilizable articulation actuator proximal to the shaft, and a distal articulable joint 22 positioned distal to the shaft 24 and proximal to an end effector in the form of a set of jaws 25. The distal articulable joint 22 is in an articulated position. The proximal portion of the device includes a housing 143 that is contiguous with a handle portion 44. The proximal portion further includes a jaw activation trigger 45 and a blade actuator member 42. The stabilizable articulation actuator is not exposed in this figure; it is included within the shaft rotator apparatus 141. In this embodiment, the end effector 25 can effect an articulation toward either side of a neutral position, the articulation angle approaching a maximum of approximately 45 degrees to either side of a neutral position. A neutral position is one in which the central longitudinal axis of the end effector is parallel to the central longitudinal axis of the shaft of the electrosurgical instrument.

The angles of articulation of the jaws with respect to the shaft are controlled by the stabilizable articulation actuator, and reflect or approximate the angles determined by operation of a lever of the stabilizable articulation actuator. Accordingly, the set of jaws may pivot to either side of a neutral position within a range of about 45 degrees, for a total pivotable range or arc of rotation of about 90 degrees. Further, in a manner determined by the stabilizable articulation actuator, the pivoting angles assumed by the set of jaws are stabilizable at spaced apart angle intervals. In some embodiments, these spaced apart angles occur at 15-degree intervals.

Figure 18:
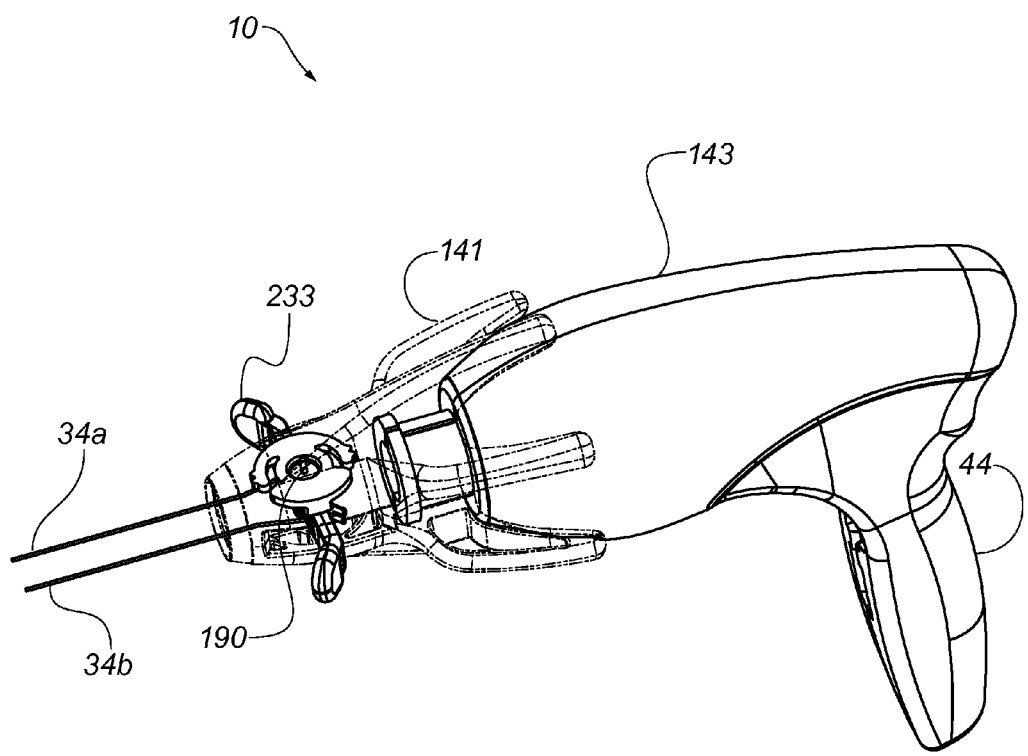
FIG. 18 is a perspective view a proximal portion of an articulable electrosurgical device depicted with a shaft rotator shown transparently, an embodiment of a stabilizable articulation actuator contained therein.

FIG. 18 is a perspective view a proximal portion of an articulable electrosurgical device 10 depicted with a shaft rotator assembly 141 shown transparently; an embodiment of a stabilizable articulation actuator 190 can be seen contained therein. Although embodiments of the device depicted in this series of figures shows the stabilizable articulation actuator included within a shaft rotator assembly, the stabilizable articulation actuator, while typically disposed at a position proximal to the shaft, it is not necessarily housed within a shaft rotator assembly.

Figure 19:
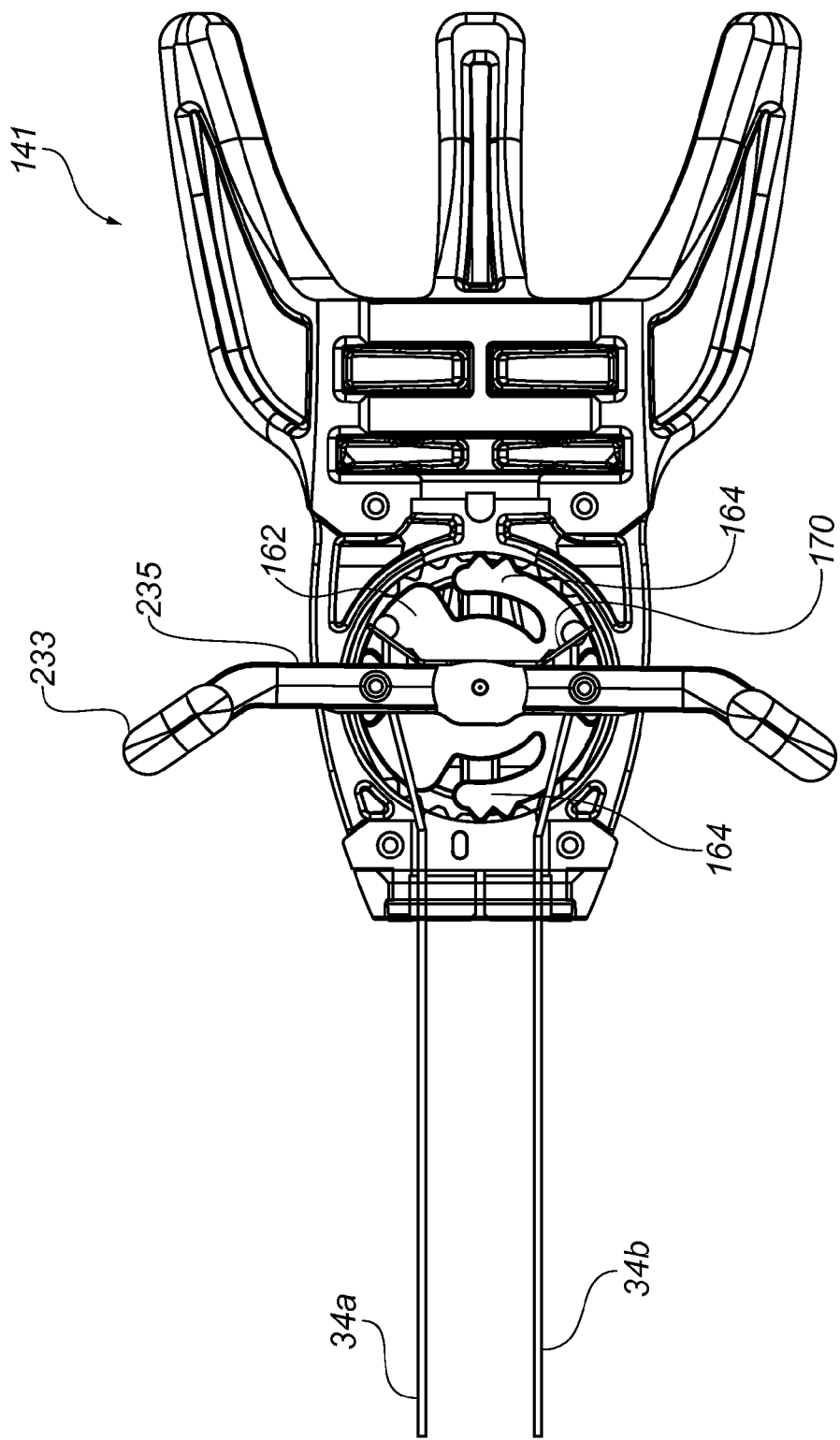
FIG. 19 is a top view, partially exposed, of a shaft rotator portion of an articulable electrosurgical device; an embodiment of a stabilizable articulation actuator contained therein is shown with a finger lever in a neutral position.

FIG. 19 is a top view, partially exposed, of a shaft rotator portion 141 of an articulable electrosurgical device 10. An embodiment of a stabilizable articulation actuator 190 is contained therein, and a finger-operable lever is shown in a neutral position. Such neutral position would hold the distal articulable joint in a neutral or non-articulated position. The proximal portions of tensioned articulating cables 34a/34b can be seen threaded through a central bar portion 235 of finger operable lever 233 and a spring plate 170 proximal to the central bar. Details of this latter arrangement are seen in figures that follow.

Figure 20:
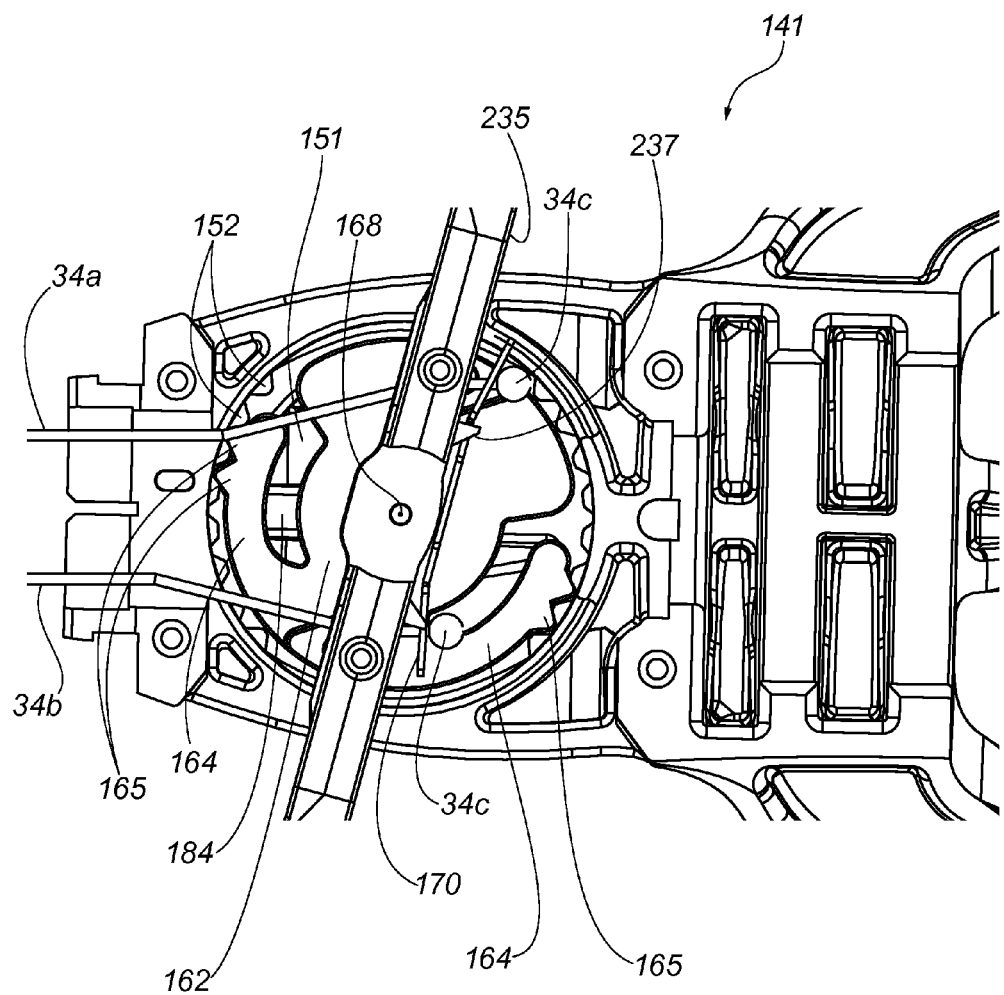
FIG. 20 is a top view, partially exposed, of a shaft rotator portion of an articulable electrosurgical device; an embodiment of a stabilizable articulation actuator contained therein is shown with a finger lever in a partially rotated position.

FIG. 20 is a partially exposed top view of a shaft rotator portion of an articulable electrosurgical device. An embodiment of a stabilizable articulation actuator is shown with a finger lever 235 in a partially rotated position. The scale of the drawing is expanded over that of FIG. 19, which allows a more detailed view of its features. Seen particularly well here are the teeth 165 disposed on the periphery of circumferentially outward-biased spring pieces or arms 164 of indexing disk 162. These teeth engage into a series of detents 152 disposed on the inner aspect of the receptacle 151. With rotation of disk 162, the spring pieces deflect inward, and then slip into the next detent available to them.

This particular embodiment of a stabilizable articulation actuator has two teeth 165 on each arm or spring piece of the indexing disk. There are two series of corresponding detents 152 on the inner aspect of the receptacle; each series has eight detents. This arrangement of teeth and corresponding detents supports a total of seven stable rotatable positions, a central neutral position, and three positions on either side of the neutral position. Embodiments of the stabilizable articulation actuator may have fewer or more teeth and fewer or more detents. Typically, however, the arrangement results in an uneven number of stable rotatable positions, i.e., a central neutral position (at zero degrees, such that the lever is at an orthogonal position with respect to the shaft) and an equal number of stable rotated positions on either side of neutral. It can be seen that the two spring piece arms are arranged circumferentially opposite each other. This arrangement creates a stable centering of inwardly directed forces, which contributes to a balanced rotational movement around central lever engagement post 168. Embodiments of the stabilizable articulation actuator include arrangements of the rotational stabilizing disk with more than two outwardly biased arms that support detent-engaging teeth, such arms generally distributed at equidistant intervals.

Embodiments of the stabilizable articulation actuator make use of a variable resistance to rotation within the available arc of rotation. Positions in an arc of rotation that require a relatively high degree of force to move through represent positions where the degree of rotation is stable, and such positions of stabilizable articulation actuator stability translate into positions of articulation angle stability at the end effector. In contrast, positions or portions of the rotational arc that provide relatively small resistance to rotation are not rotationally stable, and generally represent a rotational zone intervening between the positions of rotational stability.

In general, the arc of the rotation of the stabilizable articulation actuator is about the same as the arc of articulation of the articulable joint, and, by extension, the arc of articulation of the end effector. For example, in some of the embodiments described here, the stabilizable articulation actuator and the articulable joint/end effector all exercise movement within an arc of about 90 degrees, i.e., arcs of about 45 degrees on either side of a neutral position.

Rotation of the indexing disk 162 by the finger operable lever 235 requires a relatively large force, for example about 2 lb. pound-inches to about 15 pound-inches, in order to rotate the indexing disk out of a stable position which occurs when teeth of the indexing disk are engaged in complementary detents. Relatively little force, for example less than about 2 lb. pound-inches is required to rotate the indexing disk when teeth of the disk are in positions between detents. Even the relatively large force required to move the disk out of a stable angle position can be provided by normal levels of finger pressure, as applied to the finger operable lever. Note that the relatively large force is a characterization of the force required to rotate the indexing disk out of a stable position as being less than that required to rotate the indexing disk when its teeth are positioned between the indented aspect of the detents. Nevertheless, the relatively large force is within the range of easy operability of the finger operable lever in a manual way. Inasmuch as the mechanism can be easily pushed through a stable angle position, and inasmuch as such movement is included in normal operation of the mechanism, the stabilizable articulation actuator can be understood as a substantially non-locking system.

Figure 27:
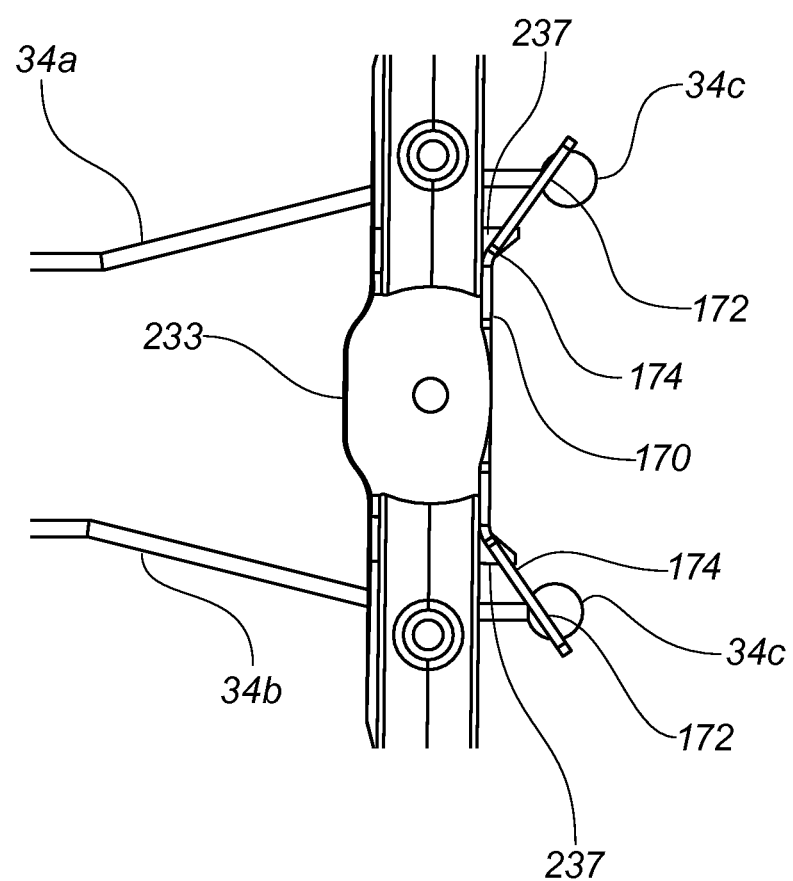
FIG. 27 is a side view of a spring plate aligned against a finger operable lever.

FIG. 20 also shows spring plate 170, as an example of a cable tensioning mechanism 170, and helps to convey an understanding of its role. In this view, disk 162 has been rotated clockwise from a neutral position such that the upper portion (per this view) of lever crossbar 235 is moved proximally, and the lower portion of the crossbar has been moved distally. By such action, the upper (by this view) cable 34a is under a relatively greater degree of tension than the lower cable 34b. In the absence of a compensatory mechanism, in this position, cable 34b would accumulate slack, and create imprecision in the actuation of articulating the articulable distal joint (not seen in this view). Spring plate 170, however, provides compensation that maintains a balance of tension between the two cables. It can be seen that the resilience of the spring plate is calibrated appropriately such that the proximal ends of cables 34a and 34b, outfitted with terminal balls 34c, are maintained at a distance from the base provided by lever crossbar 235. Further visible in this view are stabilizing tabs 237, positioned on the proximal aspect of crossbar 235. These tabs stabilize the lateral position of the spring plate during rotation. A further view of this aspect of the technology is seen in FIG. 27.

Figure 21:
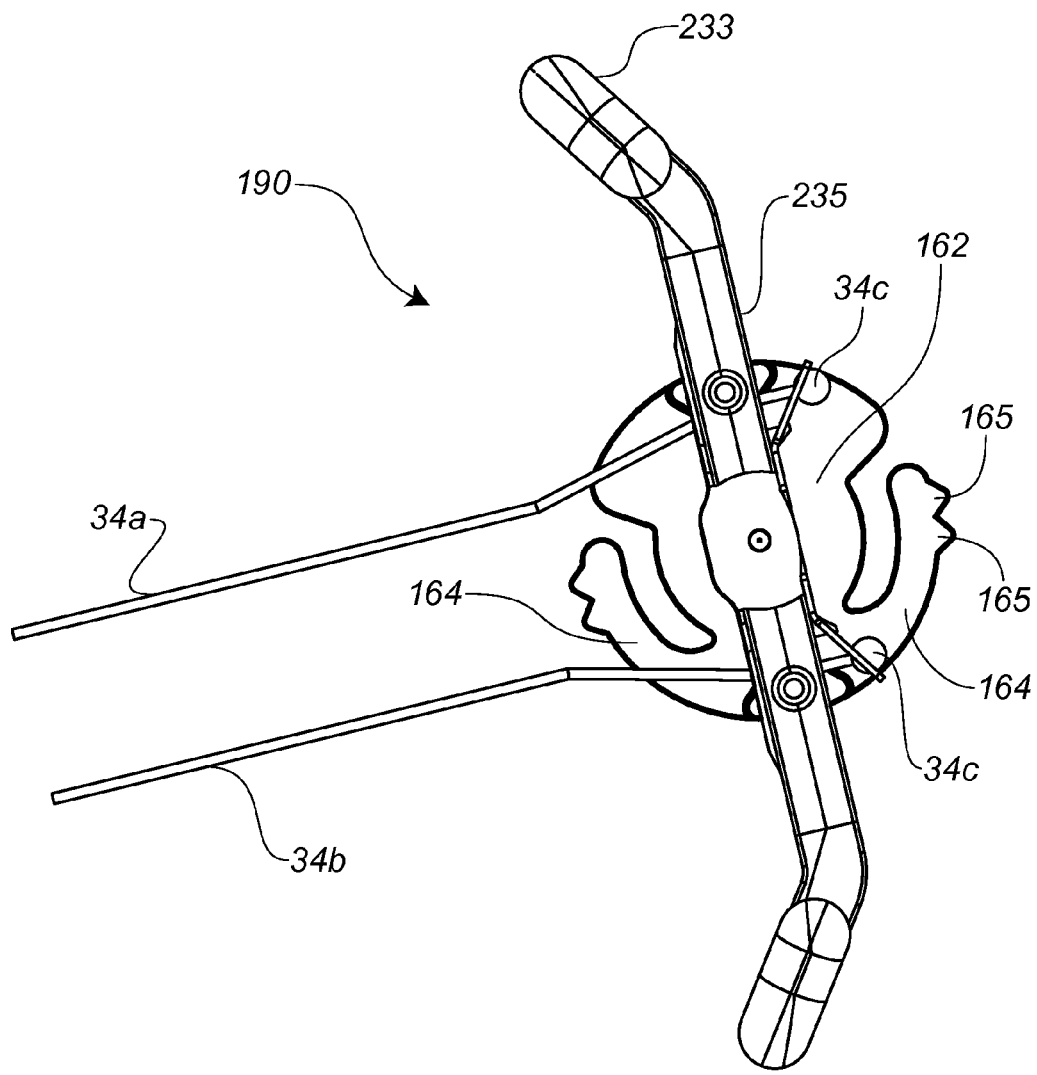
FIG. 21 is a top view of an isolated portion of a stabilizable articulation actuator showing a rotationally stabilizable disk, its finger operable lever, and force transfer cables.
Figure 22:
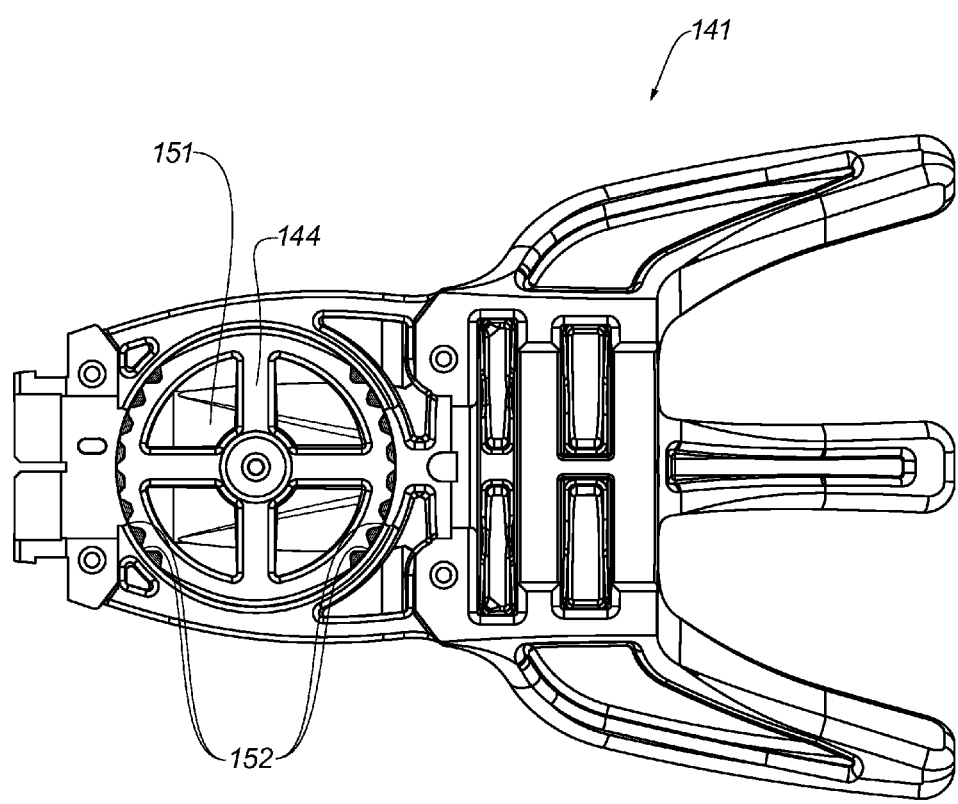
FIG. 22 is a top view with a slight proximal-looking angle of an exposed base portion of a stabilizable articulation actuator, showing the receptacle portion into which the rotationally stabilizable disk may be seated.

FIG. 21 provides a top view of an isolated portion of a stabilizable articulation actuator 190 includes a finger lever 233, indexing disk 162, and tension cables 34a and 34b. FIG. 22 provides a top view with a slight proximal-looking angle of an exposed base portion of a stabilizable articulation actuator positioned within shaft rotator 141, showing the well or receptacle portion 151 into which a rotational stabilizable disk may be seated. Cross-struts or spokes 144 are arranged across the bottom of well 151. Detents 152 are arranged on the inner aspect of the receptacle or well 151.

Figure 23:
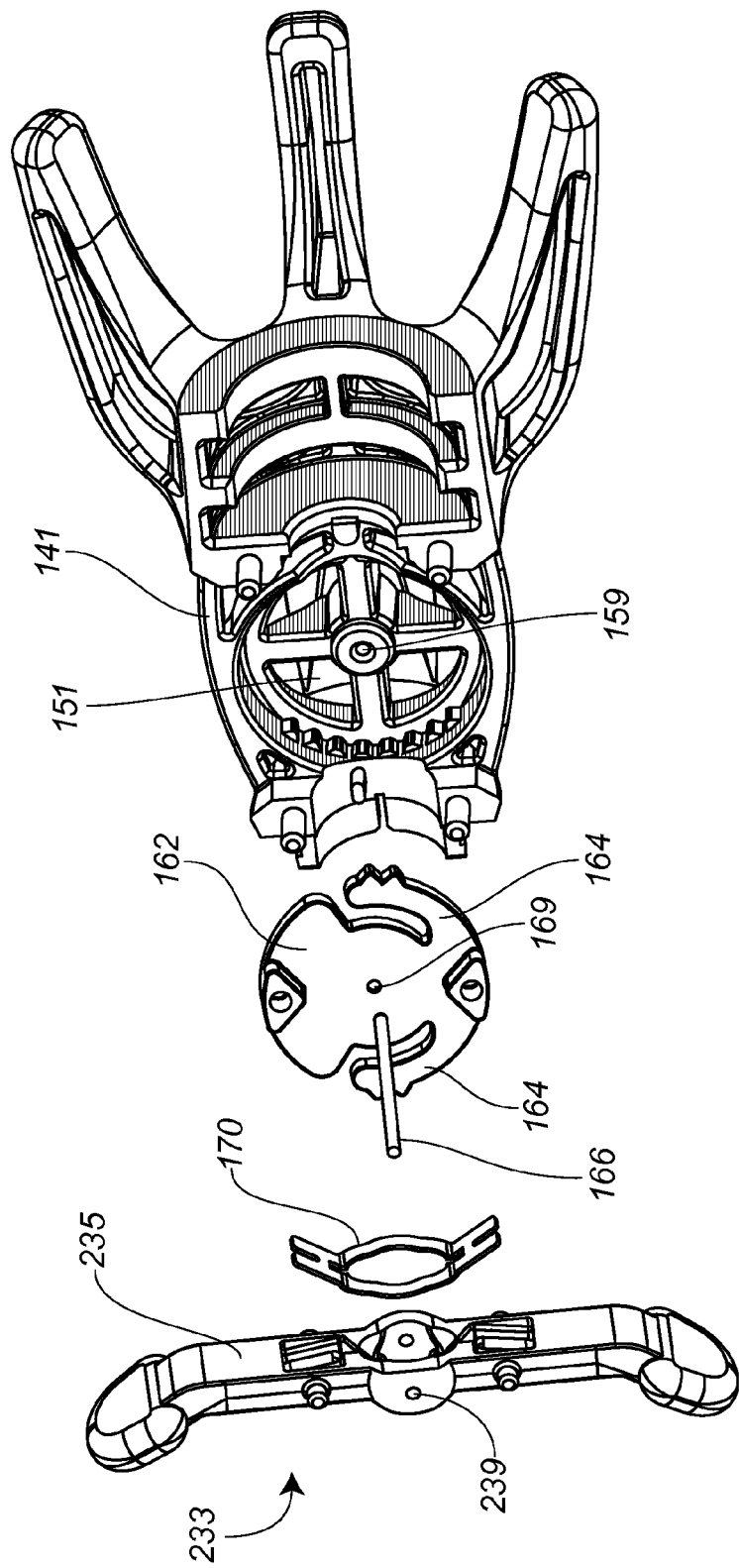
FIG. 23 is an exploded perspective view of a stabilizable articulation actuator, showing a receptacle portion into which the rotationally stabilizable disk is seated, an indexing disk, a finger operable lever to rotate the disk, and a spring plate positioned distal to the finger operable lever.

FIG. 23 is an exploded top view with a slight distal-looking perspective of a stabilizable articulation actuator, showing the arrangement by which indexing disk 162 is rotatably seated into receptacle 151, which is housed in shaft rotator 141. Finger operable lever 233 is positioned above indexing disk 162, and spring plate 170 is positioned above the disk. A central pin 166 rotatably secures disk 162 within the receptacle, and secures the attachment of finger operable lever 233 within the assembled actuator. The bottom of pin 166 is seated in the receptacle in hole 159, it passes through the indexing disk through central disk hole 169, and the top of the pin terminates within a central hole 239 in the lever.

Figure 24:
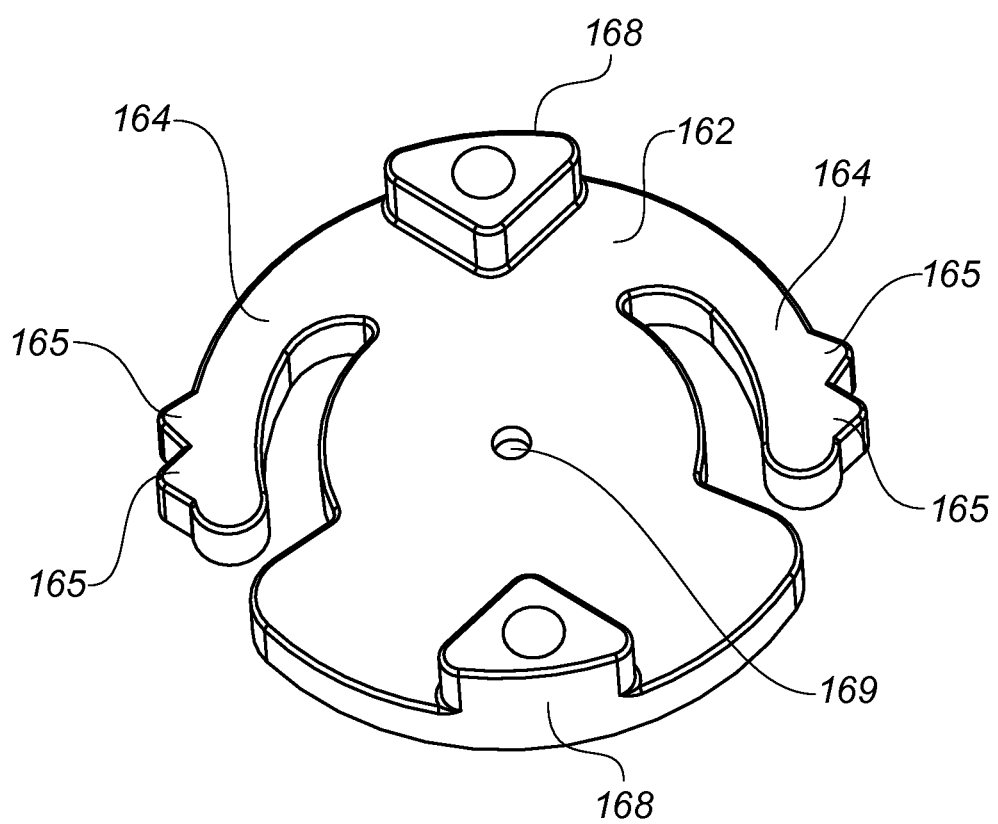
FIG. 24 is a perspective view of an indexing disk constructed; this embodiment comprises two outwardly biased spring portions.

FIG. 24 is a perspective view of an indexing or rotational position stabilizable disk 162 constructed according to aspects of the technology, this embodiment comprising two spring portions or arms 164 that are biased in a circumferentially outward direction. Teeth 165 are positioned on the periphery of spring pieces 164. A central hole is positioned to accommodate a central mounting pin (see FIG. 23). Lever engagement posts 168 are positioned on the upper surface of the disk to provide connection sites for a finger operable lever.

Figure 25:
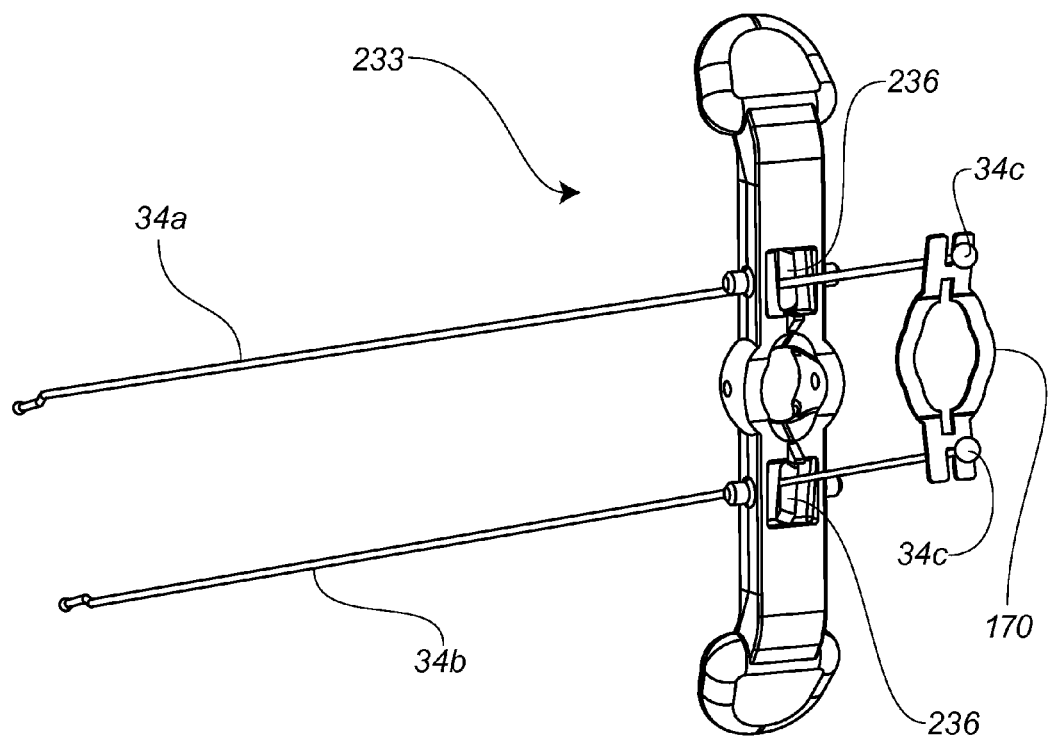
FIG. 25 is a perspective view of an isolated portion of aspects of a stabilizable articulation actuator that includes a finger operable lever, a spring plate, and actuating wires that communicate with the distally positioned articulable joint.

FIG. 25 is a perspective view of an isolated portion of the device that that shows the cooperative arrangement of a finger operable lever 233, a cable tension mechanism in the form of spring plate 170, and actuating wires 34a/34b that transit through cable transit holes 236 within the finger operable lever 233. Actuating cables 34a/34b communicate with a distally positioned articulable joint as seen in FIGS. 1, 2, 15, and 17.

Figure 26:
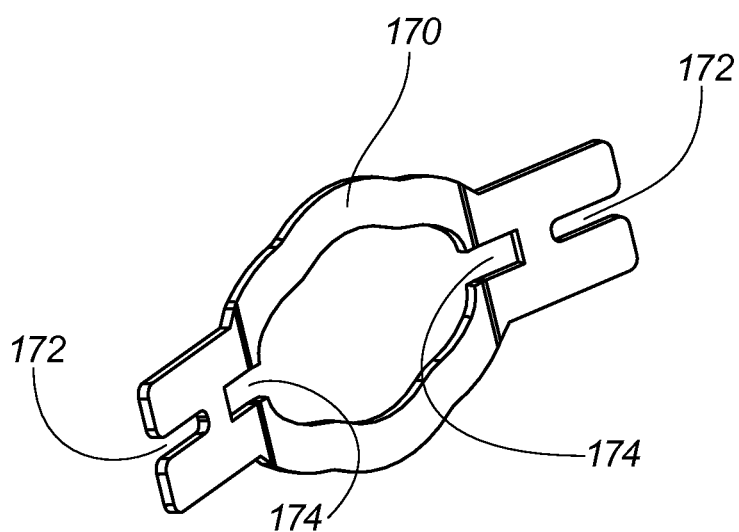
FIG. 26 is a perspective view of a spring plate portion of a stabilizable articulation actuator.

FIG. 26 is a front-facing perspective view of an aspect of a cable tensioning mechanism portion 170 of the stabilizable articulation actuator of the device. This particular embodiment of the cable tensioning mechanism comprises a spring plate with outward-facing slots 172 are configured to accommodate the proximal ends of tension cables 34a/34b, as seen in FIG. 25. Inward facing slots 174 are configured to accommodate stabilizing tabs positioned on a finger-operable lever, as seen in FIG. 27. The open-facing aspect of these slots is advantageous for ease in assembly of an electrosurgical device, and does not incur any loss of performance compared to the performance that would be provided by a circumferentially fully enclosed hole configuration.

FIG. 27 is a side view of a spring plate 170 aligned against a crossbar portion 235 of a finger operable lever. Shown in this view are stabilizing tabs 237 positioned on the proximal side of the crossbar, and inserted into inward facing slots 174. When the finger-operable lever is in a rotated position, these tabs, in position within the inward facing slots, prevent lateral slippage of the spring plate in the direction of the proximally pulled arm of the lever. This dynamic can be seen in FIG. 20, where the lower arm (in this view) of the spring plate is being held in place by a stabilizing tab against a ledge provided by an inward facing slot.

The spring plate shown in FIGS. 26 and 27 is provided as an example of a cable tensioning mechanism; the arrangement of the spring plate with the crossbar of the finger-operable lever is but one of several arrangements that are also included as embodiments of the technology. The cable tensioning mechanism may be affixed to the finger operable lever, or it may be secured to the finger operable lever in an unfixed manner, as in the illustrated embodiment, where the tension of cables 34a/34b, in conjunction with terminal balls 34c, maintains the attachment of the spring plate against the lever. Additional embodiments of the technology include finger operable lever and a cable tensioning mechanism as an integral element. The arrangement depicted FIG. 27 is advantageous in terms of ease of assembly.

Figure 28:
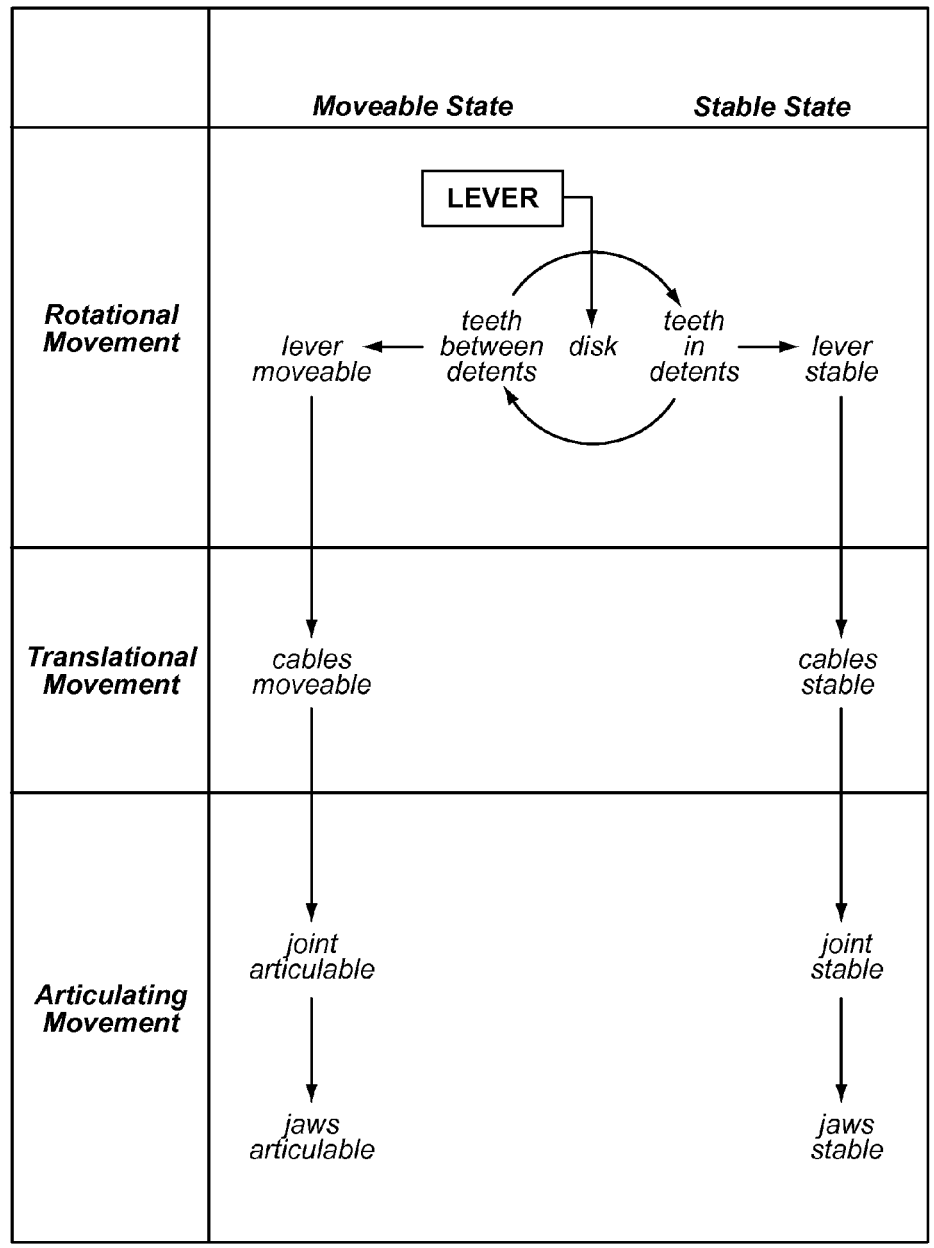
FIG. 28 is a schematic diagram of an aspect of a method for articulating an articulable joint and stabilizing it at a desired angle of articulation.

FIG. 28 is a flow diagram of an aspect of a method for articulating an articulable joint and stabilizing it at a desired angle of articulation. Steps depicted in FIG. 28 show movements that ultimately articulate an end effector, and show a transition of moveable states to stabilized states that support the end effector in a particular angle of articulation. The diagram depicts movement associated with articulation from a rotational movement of the rotational actuator, including rotation of a finger operable lever and associated rotation of a rotationally stabilizable disk, translational movement (in distal and proximal directions) of force transfer cables, and articulating movement of an articulable joint and, finally, articulating movement of a set of jaws. The rotational position of the rotationally stabilizable disk occurs within a well, and includes rotation of a set of teeth through alternating portions of a rotatable arc wherein the teeth are engaged within (engaged) or between detents (unengaged) with a series of complementary detents. A position in which the teeth are engaged in a detent (in some embodiments, two or more adjacent teeth in two or more adjacent detents) represents a stable position that manifests as a point of rotational resistance that is felt by an operator rotating the finger operable lever. The stabilization of the lever consequently stabilizes the translational movement of the force transfer cables, which in turn stabilizes the articulated angle of the articulable joint, which, in turn, stabilizes the articulated angle of the jaws.

Unless defined otherwise, all technical terms used herein have the same meanings as commonly understood by one of ordinary skill in the art of surgery, including electrosurgery. Specific methods, devices, and materials are described in this application, but any methods and materials similar or equivalent to those described herein can be used in the practice of the present technology. While embodiments of the technology have been described in some detail and by way of illustrations, such illustration is for purposes of clarity of understanding only, and is not intended to be limiting. Various terms have been used in the description to convey an understanding of the technology; it will be understood that the meaning of these various terms extends to common linguistic or grammatical variations or forms thereof. It will also be understood that when terminology referring to devices or equipment, that these terms or names are provided as contemporary examples, and the technology is not limited by such literal scope. Terminology that is introduced at a later date that may be reasonably understood as a derivative of a contemporary term or designating of a hierarchal subset embraced by a contemporary term will be understood as having been described by the now contemporary terminology. Further, while some theoretical considerations may have been advanced in furtherance of providing an understanding of the technology, the appended claims to the technology are not bound by such theory. Moreover, any one or more features of any embodiment of the technology can be combined with any one or more other features of any other embodiment of the technology, or with any technology described in the patent applications or issued patents that have been incorporated by reference, without departing from the scope of the technology. Still further, it should be understood that the technology is not limited to the embodiments that have been set forth for purposes of exemplification, but is to be defined only by a fair reading of claims appended to the patent application, including the full range of equivalency to which each element thereof is entitled.

We claim:

1. An electrosurgical instrument, comprising: an elongated shaft having an end effector associated with a distal end thereof and a handle associated with a proximal end thereof, the end effector enabled to deliver radiofrequency energy to a target site; an articulable joint positioned between the shaft and the end effector, the joint configured to articulate the end effector angularly within an arc of articulation, the articulable joint comprising at least one pivotable link positioned between a distal end of the shaft and a proximal end of the end effector; a stabilizable articulation actuator disposed proximal to the articulable joint and adapted to control the angle of articulation of the articulable joint; and at least two force transfer member portions operably connected at their proximal end to the articulation actuator, and operably connected at their distal end through the articulable joint to a proximal portion of the end effector, thereby allowing rotational movement of the articulation actuator to be translated into articulating movement of the end effector, wherein the stabilizable articulation actuator is configured to stabilize the articulable joint at a stable angle by stabilizing the force transfer member portions, the stable angle of the articulable joint being any one of a set of angles spaced apart at intervals within the arc of joint articulation, wherein the stabilizable articulation actuator comprises:
a rotationally stabilizable disk; and
a lever configured to rotate the rotationally stabilizable disk, the lever comprising two opposing arms, each arm of the lever connected to one of the at least two force transfer member portions, the lever configured such that its rotation moves a first transfer member portion in a proximal direction and a second member portion in a distal direction, wherein the stabilizable articulation actuator further comprises a force member tensioning mechanism associated with the rotatable lever, the force member tensioning mechanism configured to apply tension to the at least two force transfer members, and wherein the force member tensioning mechanism comprises a spring plate comprising two opposing arms, at least one of the at least two force transfer member portions being threaded through each arm of the rotatable lever, through the spring plate, and terminating proximal to the spring plate.

2. The instrument of claim 1, wherein the lever is a finger operable lever.

3. The instrument of claim 2, wherein the rotationally stabilizable disk and a well in which it sits are configured such that the disk can be stabilized at a position by a level of resistance to rotation of the disk that can be overcome by application of torque to the finger operable lever.

4. The instrument of claim 2, wherein the rotationally stabilizable disk and a well in which it sits are configured such that rotation of the disk through a stable position requires applying a torque to the mechanism via the finger operable lever that is greater than the torque required to rotate the disk through portions of the arc between the stable angle positions.

5. The instrument of claim 1, further comprising a shaft rotator disposed proximal to the articulable joint, the shaft rotator configured to rotate the shaft with respect to the handle, the stabilizable articulation actuator disposed within or in association with the shaft rotator.

6. The instrument of claim 1, wherein the rotationally stabilizable disk comprises at least one spring portion biased circumferentially outwardly against a wall of a circular well, a circumferentially peripheral edge of the spring portion comprising one or more teeth, the wall of the circular well comprising one or more detents, the one or more teeth and the one or more detents configured to be mutually engageable.

7. The instrument of claim 1, wherein the rotationally stabilizable disk and a well in which it sits are adapted to stabilize rotation of the disk at any one position of a set of stable positions spaced apart at intervals within an arc of disk rotation.

8. The instrument of claim 7, wherein the arc of rotation of the rotationally stabilizable disk encompasses about 90 degrees, including about 45 degrees in either direction from a neutral position wherein the finger operable lever is orthogonal to the shaft.

9. The instrument of claim 7, wherein the articulable joint is adapted to stabilize at a set of stable positions spaced apart at intervals that substantially correspond to the stable positions of the rotationally stabilizable disk.

10. The instrument of claim 1, wherein the rotationally stabilizable disk is seated in a well.

11. The instrument of claim 1, wherein the articulation actuator is further configured to stabilize the end effector at a stable angle, the stable angle of the end effector being any one of a set of angles spaced apart at intervals within the arc of end effector articulation.

12. The instrument of claim 1, wherein the at least one link of the articulable joint and the distal end of the shaft and the proximal end of the end effector comprise ball-like projections engageable in complementary grooves.

13. The instrument of claim 1, wherein the articulable joint comprises a set of two or more interconnected links positioned between the distal end of the shaft and the proximal end of the end effector.

14. The instrument of claim 1, wherein the articulable joint is configured to pivot the end effector within an arc of about 90 degrees, the 90 degree arc including about 45 degrees in either direction from a neutral position.

15. The instrument of claim 1, wherein the end effector is a set of jaws, the instrument further comprising a blade and a blade drive member collectively configured to be able to separate tissue at a target site into two portions when the tissue is being grasped by the set of jaws.

16. The instrument of claim 15, wherein the blade is configured to reside in a home position distal to the articulable joint, and to be able to move distally within the set of jaws.

17. The instrument of claim 15, wherein the blade driving member is disposed through the articulable joint, and operable in any position of articulation.

18. The instrument of claim 15, wherein the blade driving member is configured as a push and pull mechanism.

19. An electrosurgical instrument, comprising: an elongated shaft having a set of jaws associated with a distal end thereof, the set of jaws enabled to deliver radiofrequency energy to a target site; an articulable joint positioned between the shaft and the set of jaws, the joint configured to articulate the set of jaws angularly within an arc of articulation, the articulable joint comprising at least one pivotable link positioned between a distal end of the shaft and a proximal end of the set of jaws; a stabilizable articulation actuator disposed proximal to the shaft adapted to control the angle of articulation of the articulable joint; and at least two force transfer member portions operably connected at their proximal end to the articulation actuator, and operably connected at their distal end through the articulable joint to a proximal portion of the end effector, thereby allowing rotational movement of the articulation actuator to be translated into articulating movement of the end effector, wherein the stabilizable articulation actuator is configured to stabilize the articulable joint at a stable angle by stabilizing the force transfer member portions, the stable angle of the articulable joint being any one of a set of angles spaced apart at intervals within the arc of joint articulation, wherein the stabilizable articulation actuator comprises:
a rotationally stabilizable disk; and
a lever configured to rotate the rotationally stabilizable disk the lever comprising two opposing arms, each arm of the lever connected to one of the at least two force transfer member portions, the lever configured such that its rotation moves a first transfer member portion in a proximal direction and a second member portion in a distal direction, wherein the stabilizable articulation actuator further comprises a force member tensioning mechanism associated with the rotatable lever, the force member tensioning mechanism configured to apply tension to the at least two force transfer members, and wherein the force member tensioning mechanism comprises a spring plate comprising two opposing arms, at least one of the at least two force transfer member portions being threaded through each arm of the rotatable lever, through the spring plate, and terminating proximal to the spring plate.

20. An electrosurgical instrument, comprising: a set of jaws enabled to deliver radiofrequency energy to a target site; an articulable joint positioned distal to a base, the joint configured to articulate the set of jaws angularly within an arc of articulation, the articulable joint comprising at least one pivotable link positioned between the base and a proximal end of the set of jaws; a stabilizable articulation actuator disposed in association with the base and adapted to control the angle of articulation of the articulable joint; and at least two force transfer member portions operably connected at their proximal end to the articulation actuator, and operably connected at their distal end through the articulable joint to a proximal portion of the end effector, thereby allowing rotational movement of the articulation actuator to be translated into articulating movement of the end effector, wherein the stabilizable articulation actuator is configured to stabilize the articulable joint at a stable angle by stabilizing the force transfer member portions, the stable angle of the articulable joint being any one of a set of angles spaced apart at intervals within the arc of joint articulation, wherein the stabilizable articulation actuator comprises:
a rotationally stabilizable disk; and
a lever configured to rotate the rotationally stabilizable disk, the lever comprising two opposing arms, each arm of the lever connected to one of the at least two force transfer member portions, the lever configured such that its rotation moves a first transfer member portion in a proximal direction and a second member portion in a distal direction, and wherein the stabilizable articulation actuator further comprises a force member tensioning mechanism associated with the rotatable lever, the force member tensioning mechanism configured to apply tension to the at least two force transfer members, and wherein the force member tensioning mechanism comprises a spring plate comprising two opposing arms, at least one of the at least two force transfer member portions being threaded through each arm of the rotatable lever, through the spring plate, and terminating proximal to the spring plate.

21. A method of electrosurgical tissue sealing, comprising: moving a set of electrosurgical jaws of an electrosurgical instrument into a proximity of a target tissue site, the set of jaws positioned distal to an articulable joint; rotating a stabilizable articulation actuator with a finger operable lever to a desired rotational position, thereby articulating the articulable joint to a desired angle of articulation; and stabilizing the stabilizable articulation actuator in the desired rotational position, thereby stabilizing the articulable joint in the desired angle of articulation, wherein the stabilizable articulation actuator comprises: a rotationally stabilizable disk; the finger operable lever rotating the rotationally stabilizable disk, the lever comprising two opposing arms, each arm of the lever connected to one of the at least two force transfer member portions, the lever configured such that its rotation moves a first transfer member portion in a proximal direction and a second member portion in a distal direction, wherein the stabilizable articulation actuator further comprises a force member tensioning mechanism associated with the rotatable finger-operable lever, the force member tensioning mechanism configured to apply tension to the at least two force transfer members, and wherein the force member tensioning mechanism comprises a spring plate comprising two opposing arms, at least one of the at least two force transfer member portions being threaded through each arm of the rotatable finger-operable lever, through the spring plate, and terminating proximal to the spring plate.

22. The method of claim 21, wherein rotating the stabilizable articulation actuator comprises rotating the rotationally stabilizable disk.

23. The method of claim 21, wherein stabilizing the stabilizable articulation actuator comprises stabilizing the rotationally stabilizable disk.

24. The method of claim 21, further comprising articulating the set of jaws in accordance with rotating the stabilizable articulation actuator.

25. The method of claim 21, further comprising stabilizing the set of jaws in a desired angle of articulation in accordance with stabilizing the articulable joint in the desired angle of articulation.

26. The method of claim 21, wherein the desired angle of articulation of the articulable joint is one such that the jaws are in an angle such that, when closed, the jaws will grasp the target tissue.

27. The method of claim 21 further comprising rotating the finger-operable lever associated with the articulation actuator, thereby rotating the rotationally stabilizable disk.

28. The method of claim 21, further comprising driving movement of at least two force transfer member portions in accordance with rotating the rotationally stabilizable disk.

29. The method of claim 21, wherein articulating the set of jaws comprises pivoting the set of jaws within an arc of about 45 degrees in either direction from a centerline within a plane, thereby providing a total pivotable range of about 90 degrees.

30. The method of claim 21, wherein the articulable joint comprises one or more pivotable links positioned between a distal end of a shaft of the instrument and a proximal end of the jaws, and wherein articulating the articulable joint comprises pivoting the one or more pivotable links with respect to each other or with respect to the distal end of the shaft or the proximal end of the jaws.

31. The method of claim 21, wherein the jaws, when closed, have a central longitudinal axis, and wherein moving the set of jaws into the proximity of the target site comprises rotating the set of jaws about their central longitudinal axis.

32. The method of claim 21, wherein moving the set of jaws into the proximity of the target site comprises advancing the jaws through a trocar into a laparoscopic operating space.

33. The method of claim 21, wherein stabilizing the stabilizable articulation actuator comprises rotating the lever of the stabilizable articulation actuator through a portion of an arc of relatively low rotational resistance until the lever encounters a position of relatively high rotational resistance, such position being a position of articulated stability.

34. The method of claim 21, wherein stabilizing the stabilizable articulation actuator comprises rotating the lever of the stabilizable actuator through a portion of an arc that may include one or more regions of moderate rotational resistance and one or more regions of high rotational resistance, until the lever encounters a particular position of high rotational resistance wherein the jaws are in a desired position of articulation.

35. A method of articulating and stabilizing an electrosurgical end effector, wherein articulating the end effector comprises: rotating a finger operable lever; rotating a stabilizable rotatable disk; moving force transfer member portions translationally; articulating an articulable joint; and articulating the end effector; and wherein stabilizing the end effector comprises: stabilizing the stabilizable rotatable disk at a desired rotational position; stabilizing the finger operable lever at the desired rotational position; stabilizing the translation of force transfer member portions at a desired translational position; stabilizing the articulable joint at a desired angle of articulation; and stabilizing the end effector at the desired angle of articulation, wherein the stabilizable articulation actuator comprises: a rotationally stabilizable disk; the finger operable lever rotating the rotationally stabilizable disk, the lever comprising two opposing arms, each arm of the lever connected to one of the at least two force transfer member portions, the lever configured such that its rotation moves a first transfer member portion in a proximal direction and a second member portion in a distal direction, wherein the stabilizable articulation actuator further comprises a force member tensioning mechanism associated with the rotatable finger-operable lever, the force member tensioning mechanism configured to apply tension to the at least two force transfer members, and wherein the force member tensioning mechanism comprises a spring plate comprising two opposing arms, at least one of the at least two force transfer member portions being threaded through each arm of the rotatable finger-operable lever, through the spring plate, and terminating proximal to the spring plate.

\* \* \* \* \*